US011576862B2

(12) United States Patent
Kaplan et al.

(10) Patent No.: US 11,576,862 B2
(45) Date of Patent: Feb. 14, 2023

(54) METHODS AND COMPOSITIONS FOR PREPARING A SILK MICROSPHERE

(71) Applicant: Trustees of Tufts College, Medford, MA (US)

(72) Inventors: David L. Kaplan, Concord, MA (US); Tuna Yucel, Medford, MA (US); Xiaoqin Wang, Winchester, MA (US); Michael Lovett, Peabody, MA (US)

(73) Assignee: Trustees of Tufts College, Medford, MA (US)

( * ) Notice: Subject to any disclaimer, the term of this patent is extended or adjusted under 35 U.S.C. 154(b) by 276 days.

(21) Appl. No.: 15/646,601

(22) Filed: Jul. 11, 2017

(65) Prior Publication Data

US 2017/0333351 A1    Nov. 23, 2017

Related U.S. Application Data

(62) Division of application No. 14/390,356, filed as application No. PCT/US2013/036356 on Apr. 12, 2013, now abandoned.

(60) Provisional application No. 61/623,970, filed on Apr. 13, 2012.

(51) Int. Cl.
| | | |
|---|---|---|
| A61K 9/16 | (2006.01) | |
| A61K 9/00 | (2006.01) | |
| A61K 31/13 | (2006.01) | |
| C07K 16/22 | (2006.01) | |
| A61K 47/38 | (2006.01) | |

(52) U.S. Cl.
CPC .......... *A61K 9/1682* (2013.01); *A61K 9/0019* (2013.01); *A61K 9/1617* (2013.01); *A61K 9/1658* (2013.01); *A61K 31/13* (2013.01); *C07K 16/22* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,806,355 A | 2/1989 | Goosen et al. | |
| 5,015,476 A | 5/1991 | Cochrum et al. | |
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr et al. | |
| 5,591,828 A | 1/1997 | Bosslet et al. | |
| 5,902,800 A | 5/1999 | Green et al. | |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson et al. | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,690 B2 | 4/2002 | Blanchard et al. | |
| 6,387,413 B1 | 5/2002 | Miyata et al. | |
| 6,395,734 B1 | 5/2002 | Tang et al. | |
| 7,842,780 B2 | 11/2010 | Kaplan et al. | |
| 2007/0212730 A1 | 9/2007 | Vepari et al. | |
| 2009/0202614 A1 | 8/2009 | Kaplan et al. | |
| 2009/0232963 A1 | 9/2009 | Kaplan et al. | |
| 2010/0028451 A1* | 2/2010 | Kaplan ............... | A61K 9/1658 424/491 |
| 2010/0178304 A1 | 7/2010 | Wang et al. | |
| 2010/0279112 A1 | 11/2010 | Kaplan et al. | |
| 2011/0111031 A1* | 5/2011 | Jiang .................. | A61K 9/0024 424/484 |
| 2011/0171239 A1 | 7/2011 | Kaplan et al. | |
| 2015/0056294 A1 | 2/2015 | Kaplan et al. | |

FOREIGN PATENT DOCUMENTS

| | | |
|---|---|---|
| EP | 0404097 A2 | 12/1990 |
| WO | WO-1993/011161 A1 | 6/1993 |
| WO | WO-1997/008315 A1 | 3/1997 |
| WO | WO2000037547 A2 * | 11/2000 |
| WO | WO-2005/012606 A2 | 2/2005 |
| WO | WO-2006/076711 A2 | 7/2006 |
| WO | WO-2007/098951 A2 | 9/2007 |
| WO | WO-2008/118133 A2 | 10/2008 |
| WO | WO-2008/150861 A1 | 12/2008 |
| WO | WO-2010/042798 A2 | 4/2010 |
| WO | WO-2010/057142 A2 | 5/2010 |

(Continued)

OTHER PUBLICATIONS

Batzer, M.A. et al., Enhanced evolutionary PCR using oligonucleotides with inosine at the 3'-terminus, Nucleic Acids Research, 19(18): 5081 (1991).
Cao, Z. et al., The preparation of regenerated silk fibroin microspheres, Soft Matter, 3:910-915 (2007).
Chiellini, F. et al. Micro/nanostructured polymeric systems for biomedical and pharmaceutical applications, Nanomed, 3:367-93 (2008).
Chothia, C. et al., Canonical structure for the hypervariable regions of immunoglobulins, Journal of Molecular Biology, 196(4):901-917 (1987).
Extended European Search Report for EP13775182.2, 8 pages (dated Oct. 30, 2015).
Heath, C., Cells for tissue engineering, Trends Biotechnol, 18(1):17-19 (2000).

(Continued)

*Primary Examiner* — David J Blanchard
*Assistant Examiner* — Sarah J Chickos
(74) *Attorney, Agent, or Firm* — Quarles & Brady LLP

(57) ABSTRACT

Provided herein relates to methods and compositions for preparing a silk microsphere and the resulting silk microsphere. In some embodiments, the methods and compositions described herein are all aqueous, which can be used for encapsulating an active agent in a silk microsphere, while maintaining activity of the active agent during processing. In some embodiments, the resulting silk microsphere can be used for sustained delivery of an active agent encapsulated therein.

14 Claims, 6 Drawing Sheets

(56) References Cited

FOREIGN PATENT DOCUMENTS

| WO | WO-2010/141133 | | 12/2010 |
|---|---|---|---|
| WO | WO-2011/005381 | A2 | 1/2011 |
| WO | WO-2011/006133 | A2 | 1/2011 |
| WO | WO-2011/011347 | A2 | 1/2011 |
| WO | WO 2011/041395 | * | 4/2011 |
| WO | WO-2011/041395 | A2 | 4/2011 |
| WO | WO-2011/109691 | A2 | 9/2011 |
| WO | WO-2012/145739 | A1 | 10/2012 |

OTHER PUBLICATIONS

Hino, T. et al., Silk microspheres prepared by spray-drying of an aqueous system, Pharm Pharmacol Commun, 6:335-339 (2000).
Holliger, P. et al., "Diabodies": small bivalent and bispecific antibody fragments, Proc Natl Acad Sci USA, 90(14):6444-8 (1993).
International Search Report for PCT/US2013/036356, 5 pages (dated Jul. 26, 2013).
Leal-Egana, A. and Scheibel, T., Silk-based materials for biomedical applications, Biotechnol Appl Biochem, 55(3):155-167 (2010).
Li, M., et al., Study on Porous Silk Fibroin Materials. II. Preparation and Characteristics of Spongy Porous Silk Fibroin Materials, J. Appl. Poly Sci., 79:2192-2199 (2001).
Lu, Q. et al., Stabilization and release of enzymes from silk films, Macromol Biosci, 10:359-368 (2010).
Lu, S. et al., Insoluble and flexible silk films containing glycerol, Biomacromolecules, 11:143-150 (2010).
Lucas, F. et al., The Silk Fibroins, Silk Department, Shirley Institute, Manchester, England, 13:107-242 (1958).
Min, S., et al. Preparation and Characterization of Crosslinked Porous Silk Fibroin Gel, Sen'l Gakkaishi, 54(2):85-92 (1998).
Nazarov, R. et al., Porous 3-D scaffolds from regenerated silk fibroin, Biomacromolecules, 5(3):718-726 (2004).
Ohtsuka, E. et al., An Alternative Approach to Deoxyoligonucleotides as Hybridization Probes by Insertion of Deoxyinosine at Ambiguous Codon Positions, The Journal of Biological Chemistry, 260(5):2605-2608 (1985).
Omenetto, F.G. et al., New Opportunities for an Ancient Material, Science, 329:528-531 (2010).
Rajkhowa, R., et al., Reinforcing silk scaffolds with silk particles, Macromol Biosci, 10:599-611 (2010).
Rajkhowa, R., et al., Ultra-fine silk powder preparation through rotary and ball milling, Powder Technol, 185:87-95 (2008).
Rockwood, D. et al., Ingrowth of human mesenchymal stem cells into porous silk particle reinforced silk composite scaffolds: An in vitro study, Acta Biomater, 7:144-151 (2011).
Rossolini, G.M. et al., Use of Deoxyinosine-containing primers vs degenerate primers for polymerase chain reaction based on ambiguous sequence information, Molecular and Cellular Probes, 8(2):91-98 (1994).
Suckow, R. et al., Sensitive and selective liquid chromatographic assay of memantine in plasma with fluorescence detection after pre-column derivatization, J Chromatogr B Biomed Sci Appl, 729:217-224 (1999).
Takahashi, K. et. al., Induction of pluripotent stem cells from adult human fibroblasts by defined factors, *Cell*, 31(5):861-72 (2007).
Wang, et al., Growth Factor Gradients via Microsphere Delivery in Biopolymer Scaffolds for Osteochrondral Tissue Engineering, Journal of Controlled Release, 134(2):81-90 (2009).
Wang, et al., Silk Microspheres for Encapsulation and Controlled Release, Journal of Controlled Release, 117(3):360-370 (2006).
Wang, et al., Sonication-induced Gelation of Silk Fibroin for Cell Encapsulation, Biomaterials, 29(8):1054-1064 (2008).
Wang, X. et al., Silk nanospheres and microspheres from silk/pva blend films for drug delivery, Biomaterials, 31(6):1025-35 (2010).
Wenk, et al., Silk Fibroin Spheres as a Platform for Controlled Drug Delivery, Journal of Controlled Release, 132(1):26-34 (2008).
Written Opinion for PCT/US2013/036356, 6 pages (dated Jul. 26, 2013).
Ye, M. et al. Issues in long-term protein delivery using biodegradable microparticles, J Control Release, 146:241-260 (2010).
Yeo, et al., Simple Preparation and Characteristics of Silk Fibroin Microsphere, European Polymer Journal, 39:1195-1199 (2003).
Yu, et al., Induced pluripotent stem cell lines derived from human somatic cells, Science, 318:1917-1920 (2007).
Zapata, G. et al., Engineering linear F(ab')$_2$ fragments for efficient production in *Escherichia coli* and enhanced antiproliferative activity, Protein Engineering, 8(10):1057-1062 (1995).

* cited by examiner

METHODS AND COMPOSITIONS FOR PREPARING A SILK MICROSPHERE

CROSS REFERENCE TO RELATED APPLICATIONS

This Application is a Divisional Application of U.S. Non-provisional application Ser. No. 14/390,356, which was filed on Oct. 2, 2014, which is a 35 U.S.C. § 371 National Phase Entry Application of International Application No. PCT/US2013/036356 filed Apr. 12, 2013, which designates the U.S., and which claims the benefit under 35 U.S.C. § 119(e) of U.S. Provisional Application No. 61/623,970, filed Apr. 13, 2012, the contents of each of which are incorporated herein by reference in their entireties.

GOVERNMENT SUPPORT

This invention was made with government support under grant No. P41 EB002520 awarded by the National Institutes of Health (NIH). The U.S. government has certain rights in the invention.

TECHNICAL FIELD

Provided herein relates to methods and compositions for preparing a silk microsphere, and uses of the silk microsphere. In some embodiments, the silk microsphere can be used as a drug delivery vehicle or reservoir for an active agent such as a therapeutic agent.

BACKGROUND

Microspheres with a particle size from 1 to 1000 µm have been being used as drug delivery vehicles. Compared to nanospheres (e.g., <1 µm) that can more easily penetrate tissues and enter cells, microspheres possess the advantage of higher drug loading capacity due to their larger volumes. Furthermore, microspheres can also present a more homogeneous distribution of entrapped drug molecules throughout their matrices, rendering them more suitable for use as sustained drug release reservoirs. The entrapment of drug molecules is generally achieved during microsphere preparation, and the subsequent drug release commonly occurs once the dry microspheres are hydrated. See, e.g., Chiellini F. et al. "Micro/nanostructured polymeric systems for biomedical and pharmaceutical applications." Nanomed (2008) 3:367-93; Ranade V V et al. "Drug delivery systems." 2nd ed. Boca Raton; CRC Press (2004). If the microspheres are made from non-degradable materials, drug release is generally driven by diffusion alone, e.g., due to a drug concentration gradient from the microspheres to the release medium. Id. For microspheres prepared from biodegradable materials, the drug release pathways can include both material degradation and diffusion (Id.; and Ye M. et al. "Issues in long-term protein delivery using biodegradable microparticles." J Control Release (2010)146:241-260).

However, existing methods for generating microspheres generally require one or more organic solvents, and/or high temperatures. Such conditions can cause degradation or inactivation of an active agent (e.g., a therapeutic agent) during the encapsulation process, resulting in a decrease in the effective amount of the active agent available for administration to a subject. Thus, there is a need for improved methods and compositions for making a microsphere, such that an active agent can maintain its bioactivity during the encapsulation process.

SUMMARY

A low yield of microspheres and drug deactivation due to high temperatures and/or organic solvent treatments are generally the main concerns associated with the existing methods for microsphere production. Thus, these microspheres and/or fabrication methods may not be suitable for delivery of temperature-sensitive drugs, and there is a need to develop a novel method for producing microspheres that is more suitable for drug encapsulation. Provided herein generally relates to methods of preparing a silk-based material, the silk-based material resulting therefrom, and uses of the silk-based material, e.g., for drug delivery. In one embodiment, the silk-based material is produced in a form of a microsphere. Thus, methods of preparing a silk microsphere, the silk microsphere resulting therefrom, and uses of the silk microsphere, e.g., for drug delivery, are also provided herein. In some embodiments, a silk-based material (e.g., a silk microsphere) can be prepared in completely aqueous based solvents, and can thus avoid or minimize the use of organic solvents or any harsh chemicals that can degrade and/or deactivate therapeutic agent(s) loaded therein. In some embodiments, an insoluble silk-based material can be produced by the method described herein without further post-treatment with an organic solvent, e.g., methanol. In some embodiments, the silk-based material need not be exposed to a high temperature during preparation, thus maintaining bioactivity of a therapeutic agent encapsulated therein.

Inventors have developed, in some embodiments, a novel, inexpensive, quick, simple, all-aqueous method to produce a beta-sheet crystalline (water-insoluble) and porous silk-based material. For example, to prepare a silk microsphere, a silk fibroin solution can be sonicated (e.g., at a frequency of about 10 kHz or higher) to induce formation of beta-sheet structures of fibroin, and simultaneously form a spray of silk microspheres rich in beta-sheet crystalline structure. While it may not be necessary, the silk microsphere can be further freeze-dried to induce a higher degree of micro/nanoporosity. Further, the inventors have demonstrated the feasibility of such preparation methods to encapsulate a therapeutic agent (e.g., bevacizumab or memantine hydrochloride) in a silk microsphere, its injectability, and its applications for sustained delivery applications.

Accordingly, in one aspect, methods of preparing a silk microsphere are provided herein. The method comprises inducing formation of beta-sheet structure of fibroin in a silk solution; and inducing formation of a microsphere from the silk solution.

The beta-sheet structure of fibroin can be generally formed in a silk solution by any known methods in the art, e.g., but not limited to, ultrasonic energy (e.g., by sonication), shear stress, water immersion, heat treatment, solvent immersion, e.g., methanol treatment, lyophilization, gas-drying, water annealing, water vapor annealing, heat annealing, pH reduction (e.g., pH titration and/or exposing a silk solution to an electric field), or any combinations thereof. In some embodiments, e.g., where an active agent is present in the silk solution, it can be less desirable to employ heat treatment or alcohol treatment, e.g., methanol, to induce formation of beta sheet structures of fibroin. In some embodiments, formation of the beta-sheet structure of fibroin in the silk solution is induced by sonication (or a high frequency of ultrasound energy), which can be used to simultaneously form or facilitate the formation of droplets or microspheres from the silk solution.

Sonication can be generally performed at a frequency of about 10 kHz or higher, e.g., at least about 20 kHz, at least about 30 kHz, at least about 40 kHz, at least about 50 kHz, at least about 60 kHz, at least about 70 kHz, at least about 80 kHz or higher. In some embodiments, sonication can be performed at a frequency of about 20 kHz to about 40 kHz. Depending on desired morphology and/or solubility of the silk microsphere, formation of beta-sheet structure of fibroin can be induced at any sonication power output. In one embodiment, the sonication power output can range from about 1 watt to about 50 watts, or from about 2 watts to about 20 watts.

A silk microsphere can be formed from the silk solution, e.g., by atomization of the silk solution. Exemplary atomization methods can include, but are not limited to, syringe extrusion, coaxial air flow method, mechanical disturbance method, electrostatic force method, electrostatic bead generator method, spraying, sonication (ultrasonic energy), or any combinations thereof.

In one embodiment, atomization of the silk solution to form a silk microsphere can include spraying, e.g., by a spray nozzle system of a droplet generator, or through a nozzle of an air driven droplet generating encapsulation unit. In such embodiments, the shape and/or size of the silk microsphere can be adjusted by varying one or more parameters, including, without limitations, nozzle diameter, flow rate of the spray, pressure of the spray, distance of the container collecting the silk microsphere from the nozzle, concentration of the silk solution, power of sonication waves, sonication treatment time, and any combinations thereof. In some embodiments, atomization of the silk solution to form a silk microsphere can comprise ultrasonic spraying.

In some embodiments, formation of the beta-sheet structure and the microsphere can be induced simultaneously and/or concomitantly, e.g., in one single step. By way of example only, formation of the beta-sheet structure of fibroin and the microsphere in a silk solution can be induced simultaneously and/or concomitantly by flowing the silk solution through a flow-through chamber that can be ultrasonically activated. In such embodiment, the flow-through chamber can contain a nozzle for droplet generation.

A silk microsphere can be prepared in a batch process, a continuous-flow process, or a combination thereof. In some embodiments, a silk microsphere can be prepared in a continuous-flow process. For example, the silk solution can be flowed (e.g., through a flow-through chamber such as an ultrasonic atomizer) at rate of about 0.0001 mL/min to about 5 mL/min, or about 0.001 mL/min to about 5 mL/min, or about 0.05 mL/min to about 0.3 mL/min.

In some embodiments, the method can further comprise freezing the silk microsphere. For example, in one embodiment, the silk microsphere can be collected in a container maintained at a sub-zero temperature, e.g., a temperature that is sufficient to immediately freeze the silk microsphere. The container can be pre-cooled to and/or maintained at the sub-zero temperature by a cooling agent, e.g., but not limited to, dry ice, liquid nitrogen.

To induce a micro- or nano-porous structure in a silk microsphere, the method can further comprise subjecting the silk microsphere, e.g., after atomization and optional freezing, to lyophilization. The lyophilization condition (e.g., pressure and/or temperature) can affect the porosity and/or pore size of the silk microsphere. In some embodiments, the silk microsphere can be subjected to lyophilization at a condition (e.g., pressure and/or temperature) that yields a porosity of at least about 10% or more (e.g., at least about 20%, at least about 30% or more). In some embodiments, the silk microsphere can be subjected to lyophilization at a condition (e.g., pressure and/or temperature) that yields a pore size of about 1 nm to about 500 µm, or 10 nm to about 50 µm.

A silk solution for use in the method described herein can comprise fibroin at any concentration, depending on desired characteristics of the silk microsphere, e.g., drug release profile and/or its solubility, e.g., in water. In some embodiments, the silk solution can comprise silk fibroin at a concentration of about 1% (w/v) to about 30% (w/v), or about 1% (w/v) to about 15% (w/v). In one embodiment, the silk solution can comprise silk fibroin at a concentration of about 5% (w/v). In some embodiments, the silk solution can be sericin-depleted.

In some embodiments, the silk solution can further comprise one or more additives, e.g., for various desired properties. Exemplary additives can include, but are not limited to, a biopolymer, a porogen, a magnetic particle, a plasmonic particle, a metamaterial, an excipient, a plasticizer, a detection label, and any combinations thereof. The additive can be present in the silk solution at any ratio. For example, the total weight ratio of one or more additives to silk present in the silk solution can range from about 1:1000 to about 1000:1, or from about 1:100 to about 100:1, or from about 1:10 to about 10:1.

In some embodiments, the additive added into the silk solution can include one or more plasticizers, e.g., an agent that induces formation of beta-sheet crystalline structure in the silk. In such embodiments, the total weight ratio of one or more plasticizers to silk present in the silk solution can range from about 1:20 to about 20:1 or about 1:10 to about 10:1. In some embodiments, the total weight ratio of one or more plasticizers to silk present in the silk solution can be about 1:3. Non-limiting examples of a plasticizer can include glycerol, polyvinyl alcohol, collagen, gelatin, alginate, chitosan, hyaluronic acid, polyethylene glycol, polyethylene oxide, and any combinations thereof. In one embodiment, glycerol is added into the silk solution, e.g., to induce formation of beta-sheet crystalline structure in the silk.

In some embodiments, the silk microsphere described herein can be used as a drug delivery vehicle and/or reservoir for an active agent. The silk microsphere can comprise an active agent, e.g., a temperature-sensitive active agent. The active agent can be generally present in the silk microsphere in an amount of about 0.01% (w/w) to about 70% (w/w), or about 0.1% (w/w) to about 50% (w/w), or about 1% (w/w) to about 20% (w/w). The active agent can be present on a surface of the silk microsphere and/or dispersed or encapsulated in the silk microsphere homogeneously or heterogeneously or in a gradient. In some embodiments, the active agent can be added into the silk solution as an additive, prior to forming the silk microsphere. In some embodiments, the active agent can be coated on a surface of the silk microsphere after its formation. In some embodiments, a silk microsphere can be incubated in a solution of an active agent for a period of time, during which an amount of the active agent diffuses into the silk microsphere.

Depending on various applications of the silk microsphere, different types of active agents can be included in the silk microsphere. Without wishing to be bound, for example, the silk microsphere can comprise one or more therapeutic agents, including chemotherapeutic agents for treatment of a disease or disorder. Examples of the therapeutic agent can include, but are not limited to, small organic or inorganic molecules; saccharides; oligosaccharides; polysaccharides;

biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof. In one embodiment, the therapeutic agent included in a silk microsphere described herein can include bevacizumab, memantine, or a combination thereof.

In some embodiments, the method can further comprise subjecting the silk microsphere to a post-treatment. For example, while the silk microsphere produced by the methods described herein are generally water-insoluble or have a low water solubility and thus does not require additional processing to induce beta-sheet formation of fibroin, in some embodiments, the silk microsphere can be subjected to a post-treatment that is generally used to induce formation of beta-sheet crystalline structure, after the silk microsphere is formed. Such post-treatment can include, without limitations, solvent immersion, water annealing, water vapor annealing, heat annealing, or any combination thereof. In some embodiments, the method does not comprise solvent immersion, water annealing, or water vapor annealing after the silk microsphere is formed, and yet the silk microsphere is water-insoluble (e.g., maintaining original shape and volume after hydration, e.g., at about 37° C. for a period of time, e.g., for at least about 2 hours or longer) or has a lower water solubility (e.g., a water solubility of less than 50%, less than 30% or lower).

The beta-sheet crystallinity—and the resulting water insolubility, and/or the porous structure of the silk microsphere can be controlled by changing various processing condition parameters, such as sonication or flow parameters, silk concentration, the composition and/or condition of the spray solution, addition of an additive (e.g., a beta-sheet crystallinity inducing agent such as glycerol), or any combinations thereof.

In some embodiments, as noted earlier, the silk microsphere produced by the method described herein does not require a post-treatment to induce additional formation of beta-sheet crystalline structure, e.g., solvent immersion, water or water vapor annealing and/or heat annealing. In some embodiments, sonication of the silk solution can induce formation of beta-sheet crystalline structure in an amount sufficient to prepare a silk microsphere that is completely or partially insoluble in water. For example, the silk microsphere prior to the beta-sheet content-inducing post-treatment (e.g., solvent immersion, water or water vapor annealing and/or heat annealing) can have a water solubility of less than 50% or less than 30% or lower. In some embodiments, the silk microsphere prior to the beta-sheet content-inducing post-treatment (e.g., solvent immersion, water or water vapor annealing and/or heat annealing) can be water insoluble.

In some embodiments, the silk microsphere can have a beta sheet crystalline content of at least about 10%, at least about 20%, at least about 30%, at least about 40%, at least about 50%, at least about 60%, at least about 70% or higher. In some embodiments, the silk microsphere can have a beta sheet crystalline content of at least about 20%, at least about 30%, at least about 40%, at least about 50%, at least about 60%, at least about 70% or higher without any post-treatment with solvent immersion or water-vapor annealing. In some embodiments, the silk microsphere can have a beta sheet crystalline content of at least about 50% or higher without any post-treatment with solvent immersion or water-vapor annealing.

Silk microspheres described herein can be used in any applications where appropriate. For example, in some embodiments, the silk microspheres can be used as drug-delivery vehicles. In some embodiments, the silk microspheres can be used as a filling material. In some embodiments, the silk microspheres can be used in a composite material, e.g., silk microspheres encapsulated in a matrix material, e.g., a silk-based material. Accordingly, another aspect described herein relates to compositions comprising a silk microsphere prepared by various embodiments of the methods described herein. In some embodiments, the composition can be used for administration of a therapeutic agent. For in vivo administration, pharmaceutical compositions comprising a silk microsphere described herein and a pharmaceutically acceptable excipient are provided. Depending on various administration routes, in some embodiments, the composition or pharmaceutical composition can be formulated for injections.

In some embodiments of any aspects described herein, the silk microsphere can have a size of about 10 μm to about 1000 ™, or about 50 μm to about 100 μm.

In some embodiments of any aspects described herein, the silk microsphere can comprise silk in any amount. For example, the silk microsphere can comprise silk in an amount of about 10% (w/w) to about 100% (w/w), about 30% (w/w) to about 100% (w/w), or about 50% (w/w) to about 100% (w/w).

In some embodiments of any aspects described herein, the silk microsphere comprising an active agent (e.g., a therapeutic agent) can provide a sustained release of the active agent. For example, the silk microsphere comprising an active agent (e.g., a therapeutic agent) can release at least about 5% of the active agent loaded therein over a period of at least about 10 days.

In another aspect, a silk microsphere and a composition comprising one or more silk microspheres are also provided herein. For example, provide herein relates to a composition comprising a silk microsphere having a size of about 10 μm to about 2000 μm. In some embodiments, the silk microsphere is water-insoluble, e.g., having a beta sheet crystalline sheet content of at least about 50% or higher. In some embodiments, the silk microsphere further comprises a solvent-sensitive or temperature-sensitive active agent. In some embodiments, the silk microsphere can further comprise an additive as described herein, e.g., but not limited to glycerol. In some embodiments, the composition is injectable. In some embodiments, the composition is a pharmaceutical composition in a form of, e.g., but not limited to, a tablet, a capsule, lozenge, powder, paste, granules, a liquid, a solution, a gel, or any combinations thereof.

BRIEF DESCRIPTION OF THE DRAWINGS

FIG. 2A is an optical microscope image of silk SCFD microspheres before resuspension in water, where the silk SCFD microspheres were prepared from a 5% (w/v) silk solution at 25% sonication amplitude with a flow rate of about 0.1 mL/min. FIG. 2B is an optical microscope image of silk SCFD microspheres before resuspension in water, where the silk SCFD microspheres were prepared from a 5% (w/v) silk solution at 25% sonication amplitude with a flow rate of about 1 mL/min. FIG. 2C is an optical microscope image of silk SCFD microspheres after resuspension in water, where the silk SCFD microspheres were prepared from a 5% (w/v) silk solution at 25% sonication amplitude with a flow rate of about 0.1 mL/min. FIG. 2D is an optical microscope image of silk SCFD microspheres after resuspension in water, where the silk SCFD microspheres were prepared from a 5% (w/v) silk solution at 25% sonication amplitude with a flow rate of about 1 mL/min. Bar=100 µm.

FIG. 3A is an optical microscope image of silk/glycerol (in a ratio of about 3/1) SCFD spheres before suspension in water, where the silk/glycerol SCFD spheres were prepared at 25% sonication amplitude and a flow rate of 0.17 mL/min. FIG. 3B is an optical microscope image of silk/glycerol (in a ratio of about 3/1) SCFD spheres after suspension in water, where the silk/glycerol SCFD spheres were prepared at 25% sonication amplitude and a flow rate of 0.17 mL/min. Bar=100 µm.

FIGS. 4A and 4C are SEM images of silk/glycerol SCFD microspheres without memantine. FIGS. 4B and 4D are SEM images of silk/glycerol SCFD microsphere loaded with memantine. FIGS. 4A and 4B were collected from lyophilized powder. FIGS. 4C and 4D were collected from resuspended and dried powder. Bar=100 µm.

DETAILED DESCRIPTION

Figure 1:
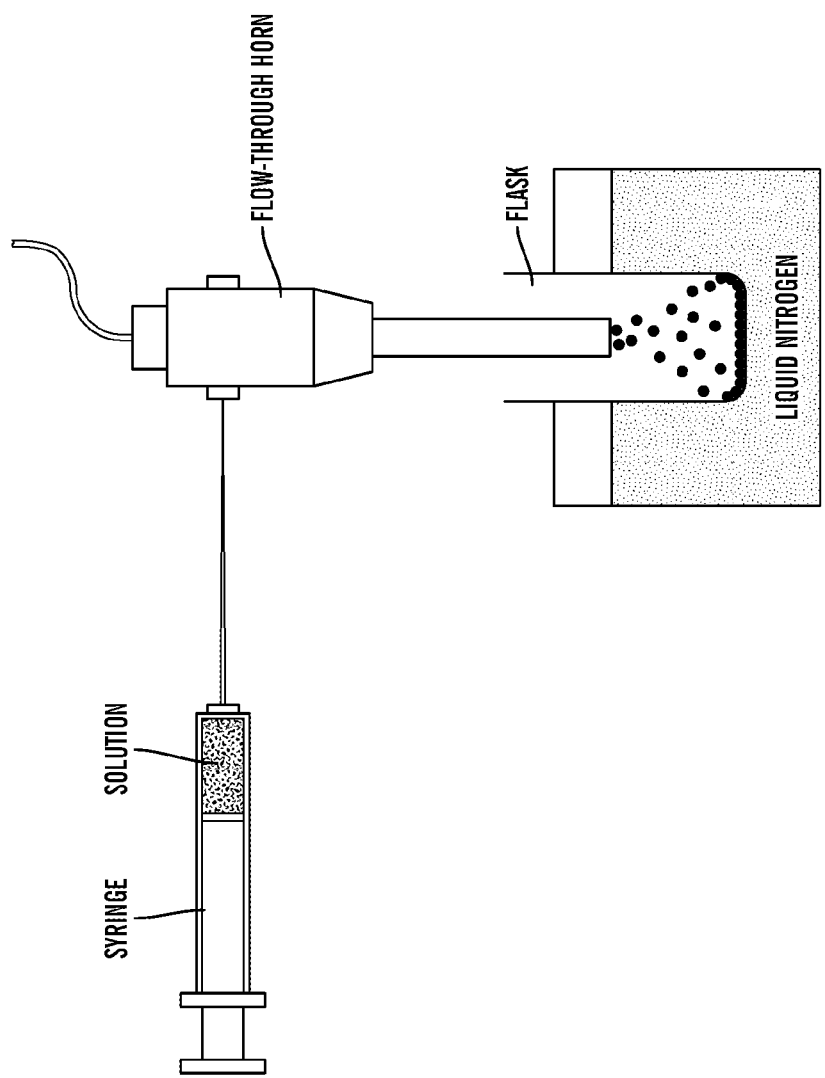
FIG. 1 is an exemplary schematic of a setup for a spray-crystallize-freeze-drying (SCFD) process for preparation of a silk microsphere.

There is a need to develop novel methods for producing higher yields of drug delivery vehicles or reservoirs, and/or methods for encapsulating a drug in those vehicles or reservoirs such that the drug can maintain its bioactivity during the encapsulating process. Provided herein generally relates to methods for preparing a silk matrix and uses thereof. In some embodiments, the silk matrix can be produced in a form of a microsphere. Thus, methods of preparing a silk microsphere, and uses of the silk microsphere, e.g., for drug delivery such as sustained release, are also provided herein. In some embodiments, an insoluble silk matrix can be produced by the method described herein without further post-treatment with an organic solvent, e.g., methanol. Additionally, a silk matrix can be prepared in completely aqueous based solvents, thus avoiding or minimizing the use of organic solvents or any harsh chemicals that can degrade or deactivate any therapeutic agent loaded therein. In other embodiments, the preparation of the silk matrix does not require a high temperature, thus allowing bioactivity of a therapeutic agent encapsulated therein to be maintained. Accordingly, the methods for increasing an effective amount of a therapeutic agent encapsulated in a silk composition are also provided herein.

The inventors have demonstrated, in some embodiments, a novel, inexpensive, simple, all-aqueous method to produce a beta-sheet crystalline (water-insoluble) and porous, silk matrix. For example, to prepare a silk microsphere, a silk fibroin solution can be sonicated for inducing formation beta-sheet structure of fibroin therein, which can be simultaneously and/or concomitantly turned into a spray of silk microsphere rich in beta-sheet crystalline structure. While it may not be necessary, the silk microsphere can be further freeze-dried to induce a higher degree of micro/nanoporosity. Further, the inventors have demonstrated the feasibility of such preparation methods to encapsulate a therapeutic agent (e.g., bevacizumab or memantine hydrochloride) in a silk microsphere, its injectability, and its applications for sustained delivery applications.

Accordingly, some embodiments of various aspects described herein relates to a silk microsphere and a composition comprising one or more silk microspheres and methods of making the same. For example, provide herein relates to a composition comprising a silk microsphere having a size of about 10 µm to about 2000 µm. In some embodiments, the silk microsphere is water-insoluble, e.g., having a beta sheet crystalline sheet content of at least about 50% or higher. In some embodiments, the silk microsphere further comprises a solvent-sensitive or temperature-sensitive active agent. In some embodiments, the silk microsphere can further comprise an additive as described herein, e.g., but not limited to glycerol. In some embodiments, the composition is injectable. In some embodiments, the composition is a pharmaceutical composition in a form of, e.g., but not limited to, a tablet, a capsule, lozenge, powder, paste, granules, a liquid, a solution, a gel, or any combinations thereof. In some embodiments, the silk microsphere is porous.

Methods for Preparing a Silk-Based Material or Silk Matrix (e.g., a Silk Microsphere) and Compositions Comprising a Silk Microsphere Accordingly, one aspect described herein relates to methods of preparing a silk-based material (or silk matrix, which is used interchangeably herein). The method comprises inducing formation of beta-sheet structure in a silk solution; and inducing formation of a silk matrix from the silk solution. In some embodiments, formation of the beta-sheet structure in a silk solution can be induced concurrently with formation of the silk matrix from the silk solution. The silk matrix can include, e.g., but are not limited to, a particle (including a microsphere and a nanosphere), a fiber, a rod, a hydrogel, a film, a gel-like or gel particle, and any combinations thereof.

Microspheres have been used widely as drug delivery vehicles in a broad range of biomedical applications. In some embodiments, the methods described herein can be used to produce a silk microsphere. Accordingly, provided herein also relates to a method of preparing a silk microsphere, the method comprising inducing formation of beta-sheet structure in a silk solution; and inducing formation of a microsphere from the silk solution.

As used interchangeably herein, the phrase "silk matrix" or "silk-based material" generally refers to a matrix including a microsphere comprising silk. A silk matrix can be present in any form, including, but not limited to, a particle or a lyophilized particle (e.g., a nanoparticle or a microparticle), a sphere or a lyophilized sphere (e.g., a nanosphere or a microsphere), a fiber, a gel or a gel-like particle, a hydrogel, a film, powder, and any combinations thereof. In some embodiments, a silk matrix can be present in a form of a microsphere or a lyophilized microsphere. In some embodiments, silk can exclude sericin. In some embodiments, silk can comprise silk fibroin, silk sericin or a combination thereof. The phrase "silk matrix" or "silk microsphere" can refer to a matrix or a microsphere in which silk (or silk fibroin) constitutes at least about 10% (w/w) or more of the total matrix, including at least at least about 20% (w/w), at least about 30% (w/w), at least about 40% (w/w), at least about 50% (w/w), at least about 60% (w/w), at least about 70% (w/w), at least about 80% (w/w), at least about 90% (w/w), at least about 95% (w/w), up to and including 100% (w/w) or any percentages between about 30% (w/w) and about 100% (w/w), of the total matrix. In certain embodiments, the silk matrix (e.g., a silk microsphere) can be substantially formed from silk or silk fibroin. In various embodiments, the silk matrix (e.g., a silk microsphere) can be substantially formed from silk or silk fibroin comprising at least one active agent.

Formation of Beta-Sheet Structure:

As used herein, the phrase "inducing formation of beta-sheet structure" refers to increasing an amount of beta-sheet structure (e.g., silk II beta-sheet crystallinity structure) in a silk solution by at least about 10%, at least about 20%, at least about 30%, at least about 40%, at least about 50%, at least about 60%, at least about 70%, at least about 80%, at least about 90% or higher, as compared to an original amount of beta-sheet structure present in the silk solution. In some embodiments, the phrase "inducing formation of beta-sheet structure" can refer to increasing an amount of beta-sheet structure in a silk solution by at least about 1-fold, at least about 2-fold, at least about 3-fold, at least about 4-fold, at least about 5-fold, or higher, as compared to an original amount of beta sheet structure present in the silk solution. Methods for determining the structure of silk protein (e.g., random coil vs. beta-sheet) are well known in the art, e.g., but not limited to, circular dichroism.

In some embodiments, formation of beta-sheet structure in a silk solution can be induced such that the silk composition (e.g., a silk microsphere) formed from the silk solution can become insoluble, e.g., without any further post-treatment described herein. By the term "insoluble" is generally meant a silk composition (e.g., a silk microsphere) completely or partially insoluble under a specified condition. Generally, solubility of a substance depends on properties and/or compositions of solvents (e.g., aqueous vs. non-aqueous solvents, and/or intermolecular interaction of the substance with a solvent), temperatures, pressures, or any combinations thereof. For example, a silk composition (e.g., a silk microsphere) can have a higher solubility in one solvent than another, and/or it can have a higher solubility in a solvent at a higher temperature than at a lower temperature in the same solvent. In some embodiments, a silk composition (e.g., a silk microsphere) can be completely or partially insoluble in an aqueous solution at a certain temperature, e.g., ranging from above 0° C. to about room temperature or from about room temperature to about body temperature of a subject (e.g., about 37° C. for a normal healthy human being, or higher or lower for other animals). An aqueous solution to which a silk composition (e.g., a silk microsphere) is exposed can include any fluid that comprises water, including, but not limited to, water, blood, interstitial fluid and any other body fluid. In some embodiments, a silk microsphere is water insoluble, e.g., being able to maintain original shape and volume after hydration, e.g., at about 37° C., for a period of time, e.g., for at least about 2 hours or longer).

The term "partially insoluble" as used herein refers to a silk composition (e.g., a silk microsphere) having a solubility with respect to a specified condition (e.g., an aqueous solution such as water or a buffered solution at room temperature) of less than 60%, less than 50%, less than 40%, less than 30%, less than 20%, less than 10%, less than 5% or lower. In some embodiments, the silk composition (e.g., a silk microsphere) can have a solubility of less than 30% in an aqueous solution such as water or a buffered solution at room temperature. In some embodiments, when the silk composition (e.g., a silk microsphere) is administered in vivo, the silk composition (e.g., a silk microsphere) dispersed or distributed in a body fluid and/or tissue can have a solubility of less than 60%, less than 50%, less than 40%, less than 30%, less than 20%, less than 10%, less than 5% or lower. As used herein, solubility expressed in percentages refers to the maximum amount of a substance that can be dissolved in ~100 g solvent to form a homogenous solution. For example, a silk microsphere having a water solubility of 30% means that a maximum amount of 30 g of silk microspheres can be dissolved in 100 g of water to form a homogenous solution.

Beta-sheet structure can be formed in a silk solution by any known methods in the art, e.g., but not limited to, sonication, shear stress, water immersion, heat treatment, alcohol treatment, e.g., methanol treatment, pH modulation, or any combinations thereof. In some embodiments, formation of the beta-sheet structure in the silk solution is not induced by heat treatment or alcohol treatment, e.g., methanol.

In some embodiments, formation of beta-sheet structure in a silk solution can be induced by sonication, e.g., sonicating a silk solution comprising silk or silk fibroin at a concentration of about 0.25% (w/v) to about 50% (w/v), about 0.25% (w/v) to about 30% (w/v), about 0.5% (w/v) to about 20% (w/v) or about 1% (w/v) to about 15% (w/v). In some embodiments, the silk solution can contain silk or silk fibroin at a concentration that allows injection, e.g., a silk concentration of about 0.5% (w/v) to about 10% (w/v). In one embodiment, the silk solution can comprise silk fibroin at a concentration of about 3% (w/v) to about 10% (w/v). In one embodiment, the silk hydrogel can comprise silk fibroin at a concentration of about 5% (w/v) to about 8% (w/v) to about silk fibroin. See, e.g., U.S. Pat. App. No. U.S. 2010/0178304 and International App. No.: WO 2008/150861, the contents of which are incorporated herein by reference, for methods of inducing beta-structure formation using sonication.

Sonication is generally an act of subjecting a substance to sound (acoustic) wave, e.g., ultrasound. Ultrasound generally spans the frequency of about 15 kHz to 10 MHz. In accordance with some embodiments of the methods described herein, the sonication can be performed at a frequency of about 10 kHz or higher (e.g., 20 kHz or higher) to induce formation of beta-sheet structure in the silk solution. In some embodiments, sonication can be performed at a frequency of about 20 kHz to about 40 kHz to induce formation of beta-sheet structure in the silk solution. The sonication can be applied to the silk solution in any fashion including, but not limited to, continuous mode, pulse mode, and any combination thereof.

Depending on desired morphology, solubility of the silk microsphere, sonication frequency, and/or sonication duration, a sonication power output of any level can be employed in inducing formation of beta-sheet structure. In some embodiments, the sonication power output can range from about 1 watt to about 50 watts, or from about 2 watts to about 20 watts. In one embodiment, the sonication power output for inducing formation of beta-sheet structure can vary from about 2 watts to about 20 watts.

The sonication or ultrasonication treatment of the silk solution can generally last for a period of time sufficient to induce formation of a desired amount of beta-sheet structure in the silk solution, but not so long as to compromise the mechanical properties of the silk matrix. Typically, depending on the sonication power output and/or frequency, sonication or ultrasonication treatment of the silk solution can last from about 5 seconds to about 60 seconds, depending on the silk concentration, amounts of fibroin in the silk solution, presence of additives, if any, and other factors appreciated by those of ordinary skill in the art. For example, the sonication or ultrasonication treatment can last from about 15 seconds to about 45 seconds. Formation of beta-sheet structure in the silk solution can generally begin at the onset of the sonication and/or ultrasonication treatment and continues for a period of time after the treatment ends.

In some embodiments, the combination of the sonication frequency, sonication duration and sonication power output used in the method of preparing a silk matrix (e.g., a silk microsphere) as described herein does not generate heat sufficient to degrade or deactivate any active agent (e.g., therapeutic agent), if any, encapsulated therein. In such embodiments, the bioactivity of an active agent (e.g., a therapeutic agent) present in the silk matrix (e.g., a microsphere) can maintain at least about 30% of its original bioactivity, including at least about 40%, at least about 50%, at least about 60%, at least about 70%, at least about 80%, at least about 90%, at least about 95% or higher, of its original bioactivity. The phrase "original bioactivity" can refer to the activity of an active agent when it is initially constituted in a silk solution prior to processing by the method described herein.

While not necessary, the sonication or ultrasonication treatment can include additional treatments to facilitate formation of beta-sheet structure in the silk solution. For example, the additional treatment can include a salt solution. Salt solutions are known in the art to assist in inducing gelation. In such embodiments, addition of a salt into a silk solution can reduce the sonication duration, frequency, and/or power output used to achieve formation of a desired amount of beta-sheet structure in the silk solution. Typical salt solutions containing ions of potassium, calcium, sodium, magnesium, copper, and/or zinc can be used. In some embodiments, potassium salt solution can be added in the silk solution for sonication treatment.

In alternative embodiments, a shear stress can also be applied to a silk solution during sonication to facilitate formation of beta-sheet structure in the silk solution. See, e.g., International App. No.: WO 2011/005381, the content of which is incorporated herein by reference for methods of producing vortex-induced silk fibroin gelation for encapsulation and delivery. In such embodiments, subjecting the silk solution to both sonication and shear stress can reduce the sonication duration, frequency, and/or power output used to achieve formation of a desired amount of beta-sheet structure in the silk solution.

Depending on stability of an active agent present in the silk solution at various pHs, in some embodiments, the pH of the silk solution prepared for sonication can be modulated. For example, the pH of the silk solution can be altered by subjecting the silk solution to an electric field and/or reducing the pH of the silk solution with an acid. See, e.g., U.S. App. No.: US 2011/0171239, the content of which is incorporated herein by reference, for details on methods of producing pH-induced silk gels. In such embodiments, subjecting the silk solution to sonication in combination with pH control can reduce the sonication duration, frequency, and/or power output used to achieve formation of a desired amount of beta-sheet structure in the silk solution.

Formation of a Microsphere from the Silk Solution:

Formation of a microsphere from the silk solution can be induced by any methods known in the art, e.g., but not limited to, emulsification, atomization, sedimentation, dispersion and precipitation methods. In emulsification, for example, the silk aqueous solution can be mixed in a non-aqueous phase containing an emulsifier to form emulsion droplets. The solution can then be gelled with a gelling agent, e.g., a pH-reducing agent or any agent that can induce silk gelation. In the dispersion method, direct dispersion of a silk solution in a cross-linking solution e.g., PEG solution, can lead to formation of microspheres. In the sedimentation/precipitation method, mixing of a silk-based ionomeric pair can lead to formation of microspheres (see, e.g., International Application No. WO 2011/109691, the content of which is incorporated herein by reference).

In some embodiments, a microsphere can be formed from the silk solution by atomization of the silk solution. Exemplary atomization methods can include, but are not limited to, syringe extrusion, coaxial air flow method, mechanical disturbance method, electrostatic force method, electrostatic bead generator method, spraying, atomization using a rotary or centrifugal atomizer, air atomization (e.g., using a spray gun and air pressure), pressure atomization, vacuum atomization (e.g., by spraying from high pressure into low pressure zone), ultrasonic atomization, sonication (ultrasonic energy), and any combinations thereof.

In air driven atomization, silk solution droplets can be broken into fine droplets with the aid of air flow pressure. The air flow pattern can be altered to form coaxial pattern for formation of uniform microspheres or particles. Coaxial air flow technique generally uses concentric streams of air which shear the liquid droplets released from one or more needles.

Alternatives to the air driven mechanism include electrostatic field, mechanical disturbance and electrostatic force. Electrostatic mechanism generally utilizes a potential difference between a capillary tip such as a nozzle and a flat counter electrode to reduce the diameter of the droplets by applying an additional force (i.e., electric force) in the direction of gravitational force in order to overcome the upward capillary force of liquid. Without wishing to be bound by theory, these methods can be used to produce droplets smaller than 100 μm from viscous liquids depending on their conductivity. In mechanical disturbance method, liquid droplets can be broken into fine droplets using a mechanical disturbance. Typically, vibrations including ultrasonic atomization can be as a mechanical disturbance to produce microspheres. In electrostatic force method, electrostatic forces can destabilize a viscous jet, where the electrostatic force can be used to disrupt the liquid surface instead of a mechanical disturbance.

Depending on various atomization method, each atomization conditions can be independently controlled to provide a desired atomized droplet size, and, in turn, a desired size of a silk microsphere. These atomization processes are known in the art and any skilled artisan can readily perform and optimize these atomization conditions for a silk solution to produce a microsphere of a desirable size.

For example, the atomization of a silk solution can produce a silk microsphere of different size and/or shape by changing instrumental/process, and/or material parameters.

Exemplary instrumental/process parameters that can be varied include, but are not limited to, air pressure of a spray, nozzle size (e.g., nozzle diameter), sonication frequency, atomization power output (e.g., sonication power output), flow rate of a spray, height of a nozzle head (e.g., distance of the nozzle head from a collection bath or container), atomization duration (e.g., sonication treatment time), and material parameters that can be varied include, but are not limited to, concentration and/or viscosity of silk solution, and/or concentration of a plasticizer, if any.

In some embodiments, the atomization of the silk solution can comprise using a spray nozzle system of a droplet generator. For example, the silk solution can be sprayed using an encapsulation unit with a desired flow rate and/or air pressure. In some embodiment, the silk solution can be sprayed through a nozzle of an air-driven droplet-generating encapsulation unit. In such embodiments, the silk solution can be sprayed with a flow rate of about 0.05 ml/hour to about 1000 ml/hour, or about 10 ml/hr to about 750 ml/hr, or about 25 ml/hr to about 500 ml/hr, or about 50 ml/hr to about 250 ml/hr. In other embodiments, the silk solution can be sprayed with a flow rate of about 1 ml/hr to about 20 ml/hr or about 5 ml/hr to about 10 ml/hr.

In some embodiments, the silk solution is sprayed using a spray nozzle system of an air-driven droplet generator with an air pressure ranging from about 0 bar-1 bar, from about 0 bar-500 mbar, from about 0 mbar-250 mbar, or from about 0 mbar-100 mbar. In some embodiments, the silk solution can be sprayed with an air pressure of about 1 bar-500 bars; or about 1 bar-250 bars; or about 5 bars-100 bars, or about 10 bars to about 50 bars.

In some embodiments, the atomization of the silk solution can comprise a spray nozzle system of an ultrasonic atomizer. Ultrasonic atomization generally relies on an electromechanical device that vibrates at a very high frequency, e.g., at about 20 kHz or higher. A silk solution passing over the vibrating surface can be turned into droplets by the high-frequency vibration, e.g., ultrasonication. In such embodiments, the sonication can be performed at a frequency of about 20 kHz or higher to form a microsphere from the silk solution. In some embodiments, the sonication can be performed at a frequency of about 20 kHz to about 10 MHz to form a microsphere from the silk solution. In some embodiments, the sonication can be performed at a frequency of about 20 kHz to about 40 kHz. The sonication can be applied to the silk solution in any fashion including, but not limited to, continuous mode, pulse mode, and any combination thereof.

Depending on desired morphology and/or solubility of the silk microsphere, sonication frequency and/or duration, a sonication power output of any level can be generally employed in atomizing a silk solution. In some embodiments, the sonication power output can range from about 1 watt to about 50 watts, or from about 2 watts to about 20 watts. In some embodiments, the sonication power output can be at least about 1 watt, at least about 2 watts, at least about 3 watts, at least about 4 watts, at least about 5 watts, at least about 10 watts, at least about 20 watts, at least about 30 watts, at least about 40 watts, at least about 50 watts, at least about 60 watts, or more. In one embodiment, the sonication power output for formation of microspheres from the silk solution can vary from about 2 watts to about 20 watts.

While formation of the beta-sheet structure in the silk solution and formation of the microsphere from the silk solution can be performed separately using different methods described herein, it can be desirable to employ the same method and/or the same instrument to achieve both purposes concomitantly. For example, in some embodiments, formation of the beta-sheet structure can be induced in the silk solution while one or more microspheres can be concomitantly or concurrently formed from the silk solution. In one embodiment, atomization and beta-sheet crystalline structure can be achieved concomitantly one single step using a single instrument. By way of example only, formation of the beta-sheet structure and atomization of the silk solution can be performed concomitantly or concurrently by flowing a silk solution through a flow-through chamber that can be ultrasonically activated. In such embodiments, the ultrasonically-activated flow-through chamber can contain a nozzle for droplet generation, e.g., an ultrasonic atomizer. Any commercial ultrasonic atomizers known in the art can be used in some embodiments of the methods described herein, including SONIFIER® cell disruptors adapted for atomization, e.g., equipped with a flow-through horn for atomization and/or spraying.

A silk microsphere can be prepared in a batch process, a continuous-flow process, or a combination thereof. In some embodiments, a silk microsphere can be prepared in a continuous-flow process. For example, when sonication is used to induce beta-sheet structure in the silk solution while concomitantly or concurrently forming microspheres from the silk solution, the flow rate of the silk solution can be adjusted to provide a sufficient residence time of the silk solution under sonication for inducing a desired amount of beta-sheet structure (that can at least partly determines solubility) and/or microspheres of desired size. For example, the silk solution can be flowed (e.g., through an ultrasonic atomizer or an equivalent thereof, e.g., a sonicator equipped with a flow-through chamber or horn) at rate of about 0.0001 mL/min to about 5 mL/min, or about 0.001 mL/min to about 5 mL/min, or about 0.05 mL/min to about 0.3 mL/min. In some embodiments, the silk solution can be flowed (e.g., through a flow-through chamber or horn) at a rate of about 0.1 mL/min to about 0.2 mL/min. One skilled in the art can readily recognize that the flow of silk solution can be accomplished by various means, including, for example, a diaphragm pump, a centrifugal pump, a gas-generation pump, a syringe pump, or by any other suitable means known to those in the art, depending on the scale of the process.

After atomization of the silk solution to form silk microspheres (e.g., by ultrasonic atomization), in some embodiments, the method can further comprise freezing the silk microspheres. Means suitable for freezing silk microspheres are known to a skilled artisan. For example, the silk microsphere can be frozen by contacting the silk microspheres, directly or indirectly, with a cooling agent. In one embodiment, the silk microspheres can be frozen by contacting them directly with a cooling agent, e.g., but not limited to, a cryogenic fluid such as liquid nitrogen, and/or dry ice; or alternatively, the silk microspheres can be collected in a pre-cooled container at a sub-zero temperature, e.g., a cryogenic temperature, which is cold enough to immediately freeze the silk microspheres. In one embodiment, the silk microspheres can be collected in a container, at least part of the outside surface of which is in contact with a cryogenic fluid such as liquid nitrogen and/or dry ice. In these embodiments, the distance between the tip of the spray nozzle and the bottom of the container can be adjusted to ensure both immediate freezing of the spray and the spray homogeneity. For example, the tip of the spray nozzle can be at least about 10 cm, at least about 20 cm, at least about 30 cm, at least about 40 cm or more, apart from the bottom of the container.

In some embodiments, the method of producing a silk microsphere can further comprise forming a porous structure in the silk microsphere. Methods for forming pores in a silk matrix are known in the art, e.g., porogen-leaching method, freeze-drying method (e.g., lyophilization), and/or gas-forming method. Such methods are described, e.g., in U.S. Pat. App. Nos.: US 2010/0279112, US 2010/0279112, and U.S. Pat. No. 7,842,780, the contents of which are incorporated herein by reference in their entirety.

In some embodiments, the silk microsphere can be subjected to lyophilization to induce a high degree of micro- or nano-porosity within the silk microsphere. In some embodiments, the silk microsphere can be frozen prior to lyophilization. The lyophilization condition (e.g., pressure and temperature) can affect the porosity and/or pore size of the silk microsphere. In some embodiments, the silk microsphere can be subjected to lyophilization at a condition (e.g., pressure and/or temperature) that yields a porosity of at least about 30%, at least about 40%, at least about 50%, at least about 60%, at least about 70%, at least about 80%, at least about 90%, or higher. Too high porosity can yield a silk composition (e.g., a silk microsphere) with lower mechanical properties, but with faster release of any active agent encapsulated therein. However, too low porosity can decrease the release of an active agent encapsulated therein. One of skill in the art can adjust the porosity accordingly, based on a number of factors such as, but not limited to, desired release rates, molecular size and/or diffusion coefficient of the active agent, and/or concentrations and/or amounts of silk fibroin in a silk matrix. The term "porosity" as used herein is a measure of void spaces in a material, e.g., a matrix such as silk fibroin, and is a fraction of volume of voids over the total volume, as a percentage between 0 and 100% (or between 0 and 1). Determination of matrix porosity is well known to a skilled artisan, e.g., using standardized techniques, such as mercury porosimetry and gas adsorption, e.g., nitrogen adsorption.

The porous silk matrix (e.g., a silk microsphere) can have any pore size, e.g., ranging from about 1 nm to about 1000 μm, from about 1 nm to about 500 μm, or from about 10 nm to about 50 μm. In some embodiments, the pores of a silk matrix (e.g., a silk microsphere) can have a size distribution or a size ranging from about 1 nm to about 1000 nm, from about 10 nm to about 750 nm, from about 25 nm to about 500 nm, from about 50 nm to about 250 nm. In other embodiments, the pores of a silk matrix (e.g., a silk microsphere) can have a size distribution or a size ranging from about 1 μm to about 1000 μm, from about 5 μm to about 750 μm, from about 10 μm to about 500 μm, from about 25 μm to about 250 μm, or from about 50 μm to about 100 μm. As used herein, the term "pore size" refers to a diameter or an effective diameter of the cross-section of a pore. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the silk fibroin can be swellable when the silk fibroin matrix is hydrated. The sizes of the pores can then change depending on the water content in the silk fibroin. The pores can be filled with a fluid such as water or air.

The porous silk matrix (e.g., a porous silk microsphere) can be used as a drug delivery vehicle or reservoir. Accordingly, in some embodiments, the silk matrix (e.g., a silk microsphere) can comprise one or more (e.g., one, two, three, four, five or more) active agents. Exemplary active agents include, but are not limited to, therapeutic agents, diagnostic agents (e.g., contrast agents), and any combinations thereof. In some embodiments, the active agent present in the silk matrix (e.g., a silk microsphere) can include a labile active agent, e.g., an agent that can undergo chemical, physical, or biological change, degradation and/or deactivation after exposure to a specified condition, e.g., high temperatures, high humidity, light exposure, and any combinations thereof. In some embodiments, the active agent present in the silk matrix (e.g., a silk microsphere) can include a temperature-sensitive active agent, e.g., an active agent that will lose at least about 30% or more, of its original activity or bioactivity, upon exposure to a temperature of at least about 10° C. or above, including at least about 15° C. or above, at least about room temperature or above, or at least about body temperature (e.g., about 37° C.) or above.

The active agent can be generally present in the silk matrix (e.g., a silk microsphere) in an amount of about 0.01% (w/w) to about 70% (w/w), or about 0.1% (w/w) to about 50% (w/w), or about 1% (w/w) to about 30% (w/w). The active agent can be present on a surface of the silk matrix (e.g., a silk microsphere) and/or encapsulated and dispersed in the silk matrix (e.g., a silk microsphere) homogeneously or heterogeneously or in a gradient. In some embodiments, the active agent can be added into the silk solution, which is then subjected to the methods described herein for preparing a silk matrix (e.g., a silk microsphere). In some embodiments, the active agent can be coated on a surface of the silk matrix (e.g., a silk microsphere). In some embodiments, the active agent can be loaded in a silk matrix (e.g., a silk microsphere) by incubating the silk microsphere in a solution of the active agent for a period of time, during which an amount of the active agent can diffuse into the silk matrix (e.g., a silk microsphere), and thus distribute within the silk matrix (e.g., a silk microsphere).

In some embodiments, the method of preparing a silk matrix (e.g., a silk microsphere) can further comprise subjecting the silk matrix (e.g., a silk microsphere) to a post-treatment, e.g., to further modify the surface and/or bulk properties of the silk matrix (e.g., a silk microsphere). In some embodiments, the post-treatment can include loading the silk matrix (e.g., a silk microsphere) with an active agent, e.g., by coating a surface of the silk matrix (e.g., a silk microsphere) with an active agent, or diffusing an active agent into the silk matrix (e.g., a silk microsphere).

In some embodiments, the post-treatment can include modifying a surface of a silk matrix (e.g., a silk microsphere). For example, the silk matrix (e.g., a silk microsphere) can be coated with an active agent as described earlier. Additionally or alternatively, the silk matrix (e.g., a silk microsphere) can be coated with a ligand, e.g., a targeting ligand, or a cell-targeting ligand. As used herein, the term "targeting ligand" refers to any material or substance which can promote targeting of the silk matrix to tissues and/or receptors in vivo and/or in vitro. The targeting ligand can be synthetic, semi-synthetic, or naturally-occurring. Materials or substances which can serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands that can be used herein include cell adhesion molecules (CAM), among which are, for example, cytokines, integrins, cadherins, immunoglobulins and selectin. The silk matrix (e.g., silk microspheres) can also encompass precursor targeting ligands. A precursor to a targeting ligand refers to any material or substance which can be converted to a targeting ligand. Such conversion can involve, for example, anchoring a precursor to a targeting ligand. Exemplary targeting precursor moieties include maleimide groups, disulfide groups, such as ortho-pyridyl disulfide, vinylsulfone groups, and azide groups. The targeting ligand can be covalently (e.g., cross-linked) or non-covalently linked to the silk matrix (e.g., silk microsphere). For example, a targeting ligand can be covalently linked to silk fibroin used for making the silk matrix.

In some embodiments, the surface of the silk matrix (e.g., a silk microsphere) can be modified, e.g., to facilitate the coating of an active agent or a ligand. Exemplary surface modification of a silk matrix (e.g., a silk microsphere) can include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347). In other embodiments, the silk matrix (e.g., a silk microsphere) can be coated with a biocompatible polymer as described herein, e.g., pegylation with a chemically active or activated derivatives of the PEG polymer (see, e.g., International Application No. WO 2010/057142). In some embodiments, the external surface of a silk matrix (e.g., a silk microsphere) can be deposited with one or more (e.g., one, two, three, four, five or more) silk matrix layers. Each silk matrix layer can have a different composition (e.g., but not limited to, different silk concentration, different drug and/or concentration). An exemplary method of stepwise deposition of one or more silk fibroin coatings around the silk matrix (e.g., a silk microsphere) can be found in U.S. App. No. US 2009/0202614, the content of which is incorporated herein by reference.

Generally, the silk matrix (e.g., a silk microsphere) produced by the method described herein need not a post-treatment to further induce formation of beta-sheet crystalline structure of fibroin in the silk matrix (e.g., a silk microsphere). For example, sonication of the silk solution can induce formation of beta-sheet crystalline fibroin sufficient to maintain the silk microsphere completely or partially insoluble in water. In some embodiments, the silk matrix (e.g., a silk microsphere) prior to the beta-sheet-inducing post-treatment (e.g., solvent immersion, water or water vapor annealing and/or heat annealing) can have a water solubility of less than 50%, less than 40%, less than 30%, less than 20%, less than 10%, less than 5%, or lower. In some embodiments, the silk microsphere prior to the beta-sheet-inducing post-treatment (e.g., solvent immersion, water or water vapor annealing and/or heat annealing) can be water-insoluble.

In some embodiments, the silk microsphere can have a beta sheet crystalline content of at least about 10%, at least about 20%, at least about 30%, at least about 40%, at least about 50%, at least about 60%, at least about 70% or higher. In some embodiments, the silk microsphere can have a beta sheet crystalline content of at least about 20%, at least about 30%, at least about 40%, at least about 50%, at least about 60%, at least about 70% or higher without any post-treatment with solvent immersion or water-vapor annealing. In some embodiments, the silk microsphere can have a beta sheet crystalline content of at least about 50% or higher without any post-treatment with solvent immersion or water-vapor annealing.

In some embodiments, the porous silk microsphere (e.g., lyophilized silk microsphere) can have a beta sheet crystalline content of at least about 20%, at least about 30%, at least about 40%, at least about 50%, at least about 60%, at least about 70% or higher without any post-treatment with solvent immersion or water-vapor annealing. In some embodiments, the porous silk microsphere (e.g., lyophilized silk microsphere) can have a beta sheet crystalline content of at least about 50% or higher without any post-treatment with solvent immersion or water-vapor annealing.

While not necessary, in some embodiments, the silk matrix (e.g., a silk microsphere) can be subjected to a post-treatment that is generally used to induce formation of beta-sheet crystalline structure of fibroin in the silk matrix (e.g., a silk microsphere). For example, in some embodiments, the silk matrix (e.g., a silk microsphere) can be subjected to a post-treatment for inducing additional formation of beta-sheet crystalline structure in the silk matrix (e.g., a silk microsphere) to further decrease the solubility of the silk matrix (e.g., a silk microsphere). Exemplary post-treatments for inducing formation of beta-sheet crystalline structure in the silk matrix (e.g., a silk microsphere) can include, but are not limited to, alcohol immersion, water vapor annealing, heat annealing, and any combinations thereof. However, in some embodiments where an active agent is present in the silk matrix (e.g., a silk microsphere), it can be undesirable to expose the silk matrix (e.g., a silk microsphere) to an organic solvent and/or high temperature, due to possibilities of degradation and/or deactivation of the active agent.

The beta-sheet crystallinity—and the resulting water insolubility, and/or the porous structure of the silk microsphere can be controlled by changing various processing condition parameters, such as sonication or flow parameters, silk concentration, the composition and/or condition of the spray solution, addition of an additive (e.g., a beta-sheet crystallinity inducing agent such as glycerol), or any combinations thereof.

Depending on the format and/or material state of the silk matrix (e.g., a silk microsphere vs. a silk fiber), the silk matrix can be of any size, ranging from nanometers in width to meters in length. In some embodiments where the silk matrix is too big in size for injection, the method can further comprise reducing the silk matrix into smaller particles, e.g., by grinding, cutting, and/or crushing. In some embodiments, the silk particles can be of any size suitable for injection.

In some embodiments where the silk matrix is a silk particle or microsphere, the silk particle or microsphere can have a dimension (e.g., a diameter) of about 0.5 µm to about 2000 µm, about 1 µm to about 2000 µm, about 10 µm to about 1000 µm, about 20 µm to about 800 µm, about 30 µm to about 500 µm, about 40 µm to about 250 µm, or about 50 µm to about 100 µm. In some embodiments, the silk microsphere can have a diameter of about 50 µm to about 100 µm. The term "microsphere" as used herein is not meant to be construed as limiting the shape of a silk particle to a sphere, but also encompasses a particle with any shape, e.g., spherical, rod, elliptical, cylindrical, capsule, or disc. It will be understood by one of ordinary skill in the art that microspheres usually exhibit a distribution of particle sizes around the indicated "size." In some embodiments, the term "size" as used herein refers to the mode of a size distribution of microspheres, i.e., the value that occurs most frequently in the size distribution. Methods for measuring the microsphere size are known to a skilled artisan, e.g., by dynamic light scattering (such as photo-correlation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

Accordingly, in another aspect, a silk microsphere and a composition comprising one or more silk microspheres are also provided herein. For example, provide herein relates to a composition comprising a silk microsphere having a size of about 10 μm to about 2000 μm. In some embodiments, the silk microsphere is water-insoluble, e.g., having a beta sheet crystalline sheet content of at least about 50% or higher. In some embodiments, the silk microsphere further can comprise a solvent-sensitive or temperature-sensitive active agent. In some embodiments, the silk microsphere can further comprise an additive as described herein, e.g., but not limited to glycerol. In some embodiments, the composition is injectable. In some embodiments, the composition can be a pharmaceutical composition in a form of, e.g., but not limited to, a tablet, a capsule, lozenge, powder, paste, granules, a liquid, a solution, a gel, or any combinations thereof, which is further described below.

Previous reports have indicated that silk microparticles, generally having irregular shapes, can be fabricated directly by milling raw or degummed silk fibers [Ref. 6]. These microparticles were used as an anti-oxidizing agent in cosmetic formulas, or as a reinforcement additive for 3D porous silk scaffolds in tissue engineering [Refs. 7,8]. For drug delivery purposes, degummed silk fibers can be solubilized in an aqueous solution into which drug is added and mixed with silk. The solution is then processed further to obtain regenerated silk materials in a variety of formats, such as films, gels, nanofibers or microspheres [Ref. 4]. However, it would be desirable to have an even distribution of the drug molecules in the silk material matrices to enable constant drug release rates.

Spray-drying, a widely used method to prepare microparticles, have been previously reported for preparing silk microspheres [Refs. 9,10]. The preparation steps for spray-dried microparticles included nozzle atomization of a silk solution, and spray drying, both steps requiring high temperatures followed by cyclonic separation [9,10]. Even these high temperatures could induce some random coil to beta-sheet transition in the microspheres and allow them to maintain their spherical shape for short periods of time (i.e., a few hours) after hydration, they are not suitable for the delivery of temperature sensitive drugs. A low yield, especially for hydrophobic polymers, and possible drug deactivation due to high temperatures and methanol treatment were the main additional concerns associated with the spray drying method. A modified spray-drying method to prepare silk microspheres was previously reported [11], in which instead of using hot air to dry the silk spray, a vibrating nozzle was used to obtain a spray, which was directly collected and frozen in a liquid nitrogen container. The vibrating nozzle was employed at a frequency far below a typical range of sonication frequency (e.g., 20 kHz-40 kHz). After lyophilization, a subsequent methanol or water vapor treatment was still necessary to keep the microspheres water insoluble. Therefore, this reported technique required exposing the silk microsphere to an organic solvent and thus lacked the potential benefits of an all-aqueous microsphere preparation method for drug delivery. In contrast to these existing and conventional spray-drying methods as previously reported, some embodiments of the method described herein require neither subjecting a silk solution to a high temperature nor post-treating a silk microsphere with methanol or water vapor for maintaining the microsphere insoluble in water. Yet beta-sheet structures can be formed in the silk microparticles (e.g., silk microspheres) produced by the method described herein and allow them to maintain their shapes for a period of time (e.g., for at least 24 hours or longer) after hydration.

Other methods to prepare silk microspheres with about 2 m average size under mild conditions using phospholipids as microsphere-forming templates have been previously described in Refs [12,13]. A method that is based on phase separation between silk and polyvinyl alcohol (PVA) has been previously described in Ref. [14], in which PVA was used as the continuous phase to separate silk droplets in the nano- to micro-scale in the blend solution, and water-insoluble silk nanospheres (300-400 nm) and microspheres (10-20 m average size) could be obtained directly by rehydration of dried blend films. However, in contrast to some embodiments of the methods described herein, none of these previously-reported methods can achieve atomization and beta-sheet crystalline formation concomitantly in one step, e.g., using a single instrument.

For example, in one particular embodiment, the method can utilize a flow-through sonication horn, through which a silk solution is passed through. A relatively high silk, beta-sheet content can be directly induced since the solution is sonicated as it passes through the horn, and a fine spray of atomized silk microparticles is obtained at the tip of the horn. The spray can be collected directly upon exiting the horn in a liquid nitrogen-cooled flask and optionally lyophilized for at least about 12 hours or longer. Subsequent freeze-drying of the spray can induce a porous structure in the microspheres with pore sizes in the nano- to microscale. Since the atomization and beta-sheet crytalline formation can be achieved concomitantly in one step using a single instrument, a minimal processing time of less than 24 hours including the lyophilization, and a low consumption of energy and solvent can be achieved, indicating that the method can be used for large-scale production of silk microspheres. Further, the silk microspheres prepared using this particular embodiment of the method described herein can have average sizes ranging from 50 to 100 m, which can be larger than the microspheres produced by the existing methods and thus broaden the available size range and provide a highly porous structural alternative for silk microspheres.

Silk Fibroin and Silk Solution for Use in the Method Described Herein:

Silk fibroin protein have unique chemical and physical properties, e.g., tunable degradation rates, controllable crystallinity due to hydrophobic beta-sheet segments—ideal diffusion barriers for entrapped drug molecules, an amino acidic nature that provides an inert microenvironment for drug encapsulation, as well as an aqueous-based material processing that is favorable for sensitive drug molecules. Silk-based biomaterials have been previously reported for their biocompatibility and biosafety for various in vivo applications, which is comparable with or superior to other biodegradable materials, such as collagen, hyaluronic acids, poly-lactic-co-glycolic acid (PLGA) [Refs. 4,5].

As used herein, the term "silk fibroin" includes silkworm fibroin and insect or spider silk protein. See e.g., Lucas et al., 13 Adv. Protein Chem. 107 (1958). Any type of silk fibroin can be used according to aspects provided herein. Silk fibroin produced by silkworms, such as *Bombyx mori*, is the most common and represents an earth-friendly, renewable resource. For instance, silk fibroin used in a silk fibroin fiber can be attained by extracting sericin from the cocoons of *B. mori*. Organic silkworm cocoons are also commercially available. There are many different silks, however, including spider silk (e.g., obtained from Nephila clavipes), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. In some embodiments, silk fibroin can be derived from other sources such as spiders, other silkworms, bees, and bioengineered variants thereof. In some embodiments, silk fibroin can be extracted from a gland of silkworm or transgenic silkworms (see, e.g., WO 2007/098951).

The silk fibroin solution can be prepared by any conventional method known to one skilled in the art. For example, *B. mori* cocoons are boiled for about 30 minutes in an aqueous solution. In one embodiment, the aqueous solution is about 0.02M $Na_2CO_3$. The cocoons are rinsed, for example, with water to extract the sericin proteins and the extracted silk is dissolved in an aqueous salt solution. Salts useful for this purpose include lithium bromide, lithium thiocyanate, calcium nitrate or other chemicals capable of solubilizing silk. In some embodiments, the extracted silk is dissolved in about 8M-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of 25%-50%. A slide-a-lyzer dialysis cassette (Pierce, MW CO 3500) can be used. However, any dialysis system may be used. The dialysis can be performed for a time period sufficient to result in a final stock concentration of aqueous silk solution between about 6% (w/v)-about 30% (w/v). In one embodiment, the dialysis can be performed for a time period sufficient to result in a final stock concentration of aqueous silk solution of about 8% (w/v). In most cases dialysis for 2-12 hours is sufficient. See, for example, International Application No. WO 2005/012606, the content of which is incorporated herein by reference.

Alternatively, the silk fibroin solution can be produced using organic solvents. Such methods have been described, for example, in Li, M., et al., J. Appl. Poly Sci. 2001, 79, 2192-2199; Min, S., et al. Sen'I Gakkaishi 1997, 54, 85-92; Nazarov, R. et al., Biomacromolecules 2004 May-June; 5(3):718-26. For example, an exemplary organic solvent that can be used to produce a silk solution includes, but is not limited to, hexafluoroisopropanol.

A silk solution subjected to the method of preparing a silk matrix (e.g., a silk microsphere) described herein can comprise fibroin at any concentration, depending on desired characteristics of the silk microsphere, e.g., drug release profile and/or its solubility, e.g., in water, and/or atomization method. In some embodiments, the silk solution can comprise silk fibroin at a concentration of about 0.1% (w/v) to about 30% (w/v), about 0.5% (w/v) to about 20% (w/v), about 1% (w/v) to about 15% (w/v), or about 2% (w/v) to about 10% (w/v). In some embodiments, the silk solution can comprise silk fibroin at a concentration of about 5% (w/v) to about 8% (w/v). In some embodiments, the silk solution can comprise silk fibroin at a concentration of about 5% (w/v). Generally, higher silk concentration can result in faster gelation. Depending on processing methods such as atomization, a high silk concentration can potentially clog a spray nozzle. A skilled artisan can optimize the silk concentration for use in various atomization methods and/or nozzle sizes.

In various embodiments, the silk fibroin can be modified for different applications and/or desired mechanical or chemical properties (e.g., to facilitate formation of a gradient of a therapeutic agent in silk fibroin matrices). One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. Patent Application. No. US 2007/0212730), diazonium coupling reaction (see, e.g., U.S. Patent Application No. US 2009/0232963), avidin-biotin interaction (see, e.g., International Application No.: WO 2011/011347) and pegylation with a chemically active or activated derivatives of the PEG polymer (see, e.g., International Application No. WO 2010/057142). Silk fibroin can also be modified through gene modification to alter functionalities of the silk protein (see, e.g., International Application No. WO 2011/006133). For instance, the silk fibroin can be genetically modified, which can provide for further modification of the silk such as the inclusion of a fusion polypeptide comprising a fibrous protein domain and a mineralization domain, which can be used to form an organic-inorganic composite. See WO 2006/076711. In some embodiments, the silk fibroin can be genetically modified to be fused with a protein, e.g., a therapeutic protein. Additionally, the silk fibroin matrix can be combined with a chemical, such as glycerol, that, e.g., affects flexibility and/or solubility of the matrix. See, e.g., WO 2010/042798, Modified Silk films Containing Glycerol.

In some embodiments, the silk solution for preparing a silk matrix (e.g., a silk microsphere) can further comprise one or more (e.g., one, two, three, four, five or more) additives, e.g., for various desired properties and/or applications. Exemplary additives can include, but are not limited to, a biopolymer, a porogen (e.g., a salt or polymeric particle), a magnetic particle, a plasmonic particle, a metamaterial, an excipient, a plasticizer, a detection label, and any combinations thereof. The additive(s) can be present in the silk solution at any ratio. For example, the weight ratio of the additive to silk in the silk solution can range from about 1:1000 to about 1000:1, or from about 1:100 to about 100:1, or from about 1:10 to about 10:1. In some embodiments, total amount of additives in the solution can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the solution.

In some embodiments, at least one additive added into the silk solution can include one or more (e.g., one, two, three, four, five or more) plasticizers, e.g., agent(s) that induce formation of beta-sheet crystalline structure in the silk. In such embodiments, the total weight ratio of the plasticizer(s) to silk in the silk solution can range from about 1:20 to about 20:1 or about 1:10 to about 10:1. In some embodiments, the total weight ratio of the plasticizer(s) to silk in the silk solution can be about 1:3. In some embodiments, the total amount of the plasticizer(s) can be from about 10 wt % to about 50 wt %, from about 20 wt % to about 40 wt %, or from about 25 wt % to about 35 wt %, of the total silk fibroin in the solution. Non-limiting examples of a plasticizer can include glycerol, polyvinyl alcohol, collagen, gelatin, alginate, chitosan, hyaluronic acid, polyethylene glycol, polyethylene oxide, and any combinations thereof. In one embodiment, glycerol is added into the silk solution, e.g., to induce formation of beta-sheet crystalline structure in the silk. In such embodiments, the weight ratio of glycerol to silk in the silk solution can range from about 1:10 to about 10:1. In one embodiment, the weight ratio of glycerol to silk in the silk solution can be about 1:3. State another way, the amount of glycerol in the solution can be about 20 wt % to about 40 wt %, or from about 25 wt % to about 35 wt %, of the total silk fibroin in the solution.

In some embodiments, the amount of a plasticizer (e.g., glycerol) added into the silk solution can be sufficient to induce, during sonication, formation of a silk II beta-sheet crystallinity content of at least about 5%, for example, a silk II beta-sheet crystallinity content of at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation), in the silk solution. In some embodiments, the silk in the silk matrix can be completely in a silk II beta-sheet conformation after the silk solution is atomized into a silk microsphere.

In some embodiments, at least one additive added into the silk solution for preparing a silk matrix, e.g., a silk microsphere, can include one or more (e.g., one, two, three, four, five or more) biopolymers and/or biocompatible polymers. Exemplary biopolymers and/or biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly (ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; 387,413; 6,325,810; 6,337,198; 6,267,776; 5,576,881; 6,245,537; 5,902,800; and 5,270,419, content of all of which is incorporated herein by reference.

Exemplary Therapeutic Agents and Amounts Thereof in Silk Matrices, e.g., Microspheres Depending on various applications of the silk matrix (e.g., a silk microsphere), different types of the active agent can be present in the silk matrix (e.g., a silk microsphere), e.g., by encapsulation and/or coating. Without wishing to be bound, for example, the silk matrix (e.g., a silk microsphere) can comprise one or more active agents, including, but not limited to, therapeutic agents, imaging agents or any combinations thereof.

In some embodiments, one or more imaging agents can be included in a silk matrix (e.g., a silk microsphere). Examples of imaging agents can include, but are not limited to, dyes, fluorescent agents, radiological imaging agents, any art-recognized contrast agents for imaging tissues and/or organs, and any combinations thereof. Fluorescent agents are well known in the art. Examples of fluorescent agents can include, but are not limited to, fluoresceinisothiocyanato-dextran (FITC-dextran), ruthenium based dye, or platinum porphyrin, or a mixture thereof.

As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk matrix (e.g., a silk microsphere) can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an antiinflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as *senna* concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

As noted above, any therapeutic agent can be included in a silk matrix (e.g., a silk microsphere), e.g., by encapsulation and/or coating. In some embodiments, it is desirable to include in a silk matrix (e.g., a silk microsphere) materials to promote the growth of the agent (for biological agents), promote the functionality of the agent after it is released from the encapsulation, or increase the agent's ability to survive or retain its efficacy during the encapsulation period. Materials known to promote cell growth include cell growth media, such as Dulbecco's Modified Eagle Medium (DMEM), fetal bovine serum (FBS), non-essential amino acids and antibiotics, and growth and morphogen factors such as basic fibroblast growth factor (bFGF), transforming growth factors (TGFs), Vascular endothelial growth factor (VEGF), insulin-like growth factor (IGF-I), bone morphogenetic growth factors (BMPs), nerve growth factors and related proteins.

Additional options for delivery via the silk matrix (e.g., a silk microsphere) described herein can include DNA, siRNA, antisense, plasmids, liposomes and related systems for delivery of genetic materials; antibodies and antigen binding fragment thereof; peptides and proteins to active cellular signaling cascades; peptides and proteins to promote mineralization or related events from cells; adhesion peptides and proteins to improve gel-tissue interfaces; antimicrobial peptides; and proteins and related compounds.

In some embodiments, the therapeutic agent(s) for use in the present disclosure include, but are not limited to, those requiring relatively frequent dosing. For example, those used in the treatment of chronic disorders or conditions.

In some embodiments, the therapeutic agent includes 2-[4-[3-[2-(trifluoromethyl)-10H-phenothiazin-10-yl]propyl]piperazin-1-yl]ethanol (fluphenazine), 3,5-dimethyltricyclo[3.3.1.1]decan-1amine (3,5-dimethyladamantan-1-amine, memantine) or memantine chloride. Fluphenazine is presently available in oral and injectable dosage forms. Disadvantageously, fluphenazine has an incomplete oral bioavailability of 40% to 50% (due to extensive first pass metabolization in the liver) such that its half-life is 15 to 30 hours. Memantine is presently available in oral dosage form as tablets, capsules or solution, under the brand Namenda by Forest Labs. In some embodiment, memantine can be administered or included in the silk matrix (e.g., a silk microsphere) in combination with one or more cholinesterase inhibitors (e.g., donepezil, razadyne and rivastigmin).

In some embodiments, the therapeutic agent includes bevacizumab (AVASTIN®), ranibizumab (LUCENTIS®), or a combination thereof. In some embodiments, bevacizumab and/or ranibizumab can be administered or included in the silk matrix (e.g., a silk microsphere) in combination with one or more antiangiogenic agents known in the art, e.g., anti-VEGF agents.

In some embodiments, the therapeutic agent is a cell, e.g. a biological cell. In such embodiments, the cells can be distributed within a silk matrix (e.g., a silk microsphere) by incubating the silk matrix (e.g., a silk microsphere) in a cell suspension, where the cells can migrate from the suspension into the pores of the silk matrix (e.g., a silk microsphere). Cells amenable to be incorporated into the silk matrix (e.g., a silk microsphere) include, but are not limited to, stem cells (embryonic stem cells, mesenchymal stem cells, bone-marrow derived stem cells and hematopoietic stem cells), chondrocytes progenitor cells, pancreatic progenitor cells, myoblasts, fibroblasts, keratinocytes, neuronal cells, glial cells, astrocytes, pre-adipocytes, adipocytes, vascular endothelial cells, hair follicular stem cells, endothelial progenitor cells, mesenchymal cells, neural stem cells and smooth muscle progenitor cells.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science*, 2007, 318, 1917-1920 and Takahashi K. et. al., *Cell*, 2007, 131, 1-12).

Cells useful for incorporation into the silk matrix (e.g., a silk microsphere) can come from any source, for example human, rat or mouse. Human cells include, but are not limited to, human cardiac myocytes-adult (HCMa), human dermal fibroblasts-fetal (HDF-f), human epidermal keratinocytes (HEK), human mesenchymal stem cells-bone marrow, human umbilical mesenchymal stem cells, human hair follicular inner root sheath cells, human umbilical vein endothelial cells (HUVEC), and human umbilical vein smooth muscle cells (HUVSMC), human endothelial progenitor cells, human myoblasts, human capillary endothelial cells, and human neural stem cells.

Exemplary rat and mouse cells include, but not limited to, RN-h (rat neurons-hippocampal), RN-c (rat neurons-cortical), RA (rat astrocytes), rat dorsal root ganglion cells, rat neuroprogenitor cells, mouse embryonic stem cells (mESC) mouse neural precursor cells, mouse pancreatic progenitor cells mouse mesenchymal cells and mouse endodermal cells.

In some embodiments, tissue culture cell lines can be used in the silk matrix (e.g., a silk microsphere) described herein. Examples of cell lines include, but are not limited to, C166 cells (embryonic day 12 mouse yolk), C6 glioma Cell line, HL1 (cardiac muscle cell line), AML12 (nontransforming hepatocytes), HeLa cells (cervical cancer cell line) and Chinese Hamster Ovary cells (CHO cells).

An ordinary skill artisan in the art can locate, isolate and expand such cells. In addition, the basic principles of cell culture and methods of locating, isolation and expansion and preparing cells for tissue engineering are described in "Culture of Cells for Tissue Engineering" Editor(s): Gordana Vunjak-Novakovic, R. Ian Freshney, 2006 John Wiley & Sons, Inc., and Heath C. A., *Trends in Biotechnology*, 2000, 18, 17-19, content of both of which is herein incorporated by reference in its entirety.

Generally, any amount of the therapeutic agent can be dispersed or encapsulated in the silk matrix, depending on a number of factors, including, but not limited to, desirable release profile (e.g., release rates and/or duration), properties (e.g., half-life and/or molecular size) and/or potency of the therapeutic agent, severity of a subject's disease or disorder to be treated, desirable administration schedule, loading capacity of the silk matrix, and any combinations thereof. For example, in some embodiments, a therapeutic agent can be present in a silk matrix (e.g., about 10 mg of silk microspheres) in an amount of about 1 ng to about 100 mg, about 500 ng to about 90 mg, about 1 µg to about 75 mg, about 0.01 mg to about 50 mg, about 0.1 mg to about 50 mg, about 1 mg to about 40 mg, about 5 mg to about 25 mg. In some embodiments, a therapeutic agent can be present in a silk matrix (e.g., about 10 mg of silk microspheres) in an amount of about 0.01% (w/w) to about 90% (w/w) of the total weight (i.e., the combined weight of the silk matrix and the therapeutic agent), for example, including, about 0.01% (w/w) to about 70% (w/w), about 0.1% (w/w) to about 50% (w/w), about 1% (w/w) to about 30% (w/w), about 5% (w/w) to about 25% (w/w), or about 7.5% (w/w) to about 20 (w/w) of the total weight. In some embodiments, the therapeutic agent can be present in a silk matrix in an amount of about 0.5% (w/w) to about 20% (w/w) of the total weight. In some embodiments, the therapeutic agent can be present in a silk matrix in an amount of about 2% (w/w) to about 20% (w/w) of the total weight. In one embodiment, the therapeutic agent (e.g., bevacizumab, ranibizumab, or a mixture thereof) can be present in a silk matrix in an amount of about 1% (w/w) to about 20% (w/w) of the total weight. In one embodiment, the therapeutic agent (e.g., memantine) can be present in a silk matrix in an amount of about 0.1% (w/w) to 5% (w/w) of the total weight.

Without wishing to be bound by theory, the duration of a therapeutic effect on a target site to be treated is generally correlated with how long an amount of the therapeutic agent delivered to the target site can be maintained at a therapeutically effective amount. Thus, in some embodiments, a pharmaceutical composition described herein can comprise a therapeutic agent dispersed or encapsulated in a silk matrix (e.g., a dosage of silk microspheres), wherein the therapeutic agent is present in an amount sufficient to maintain a therapeutically effective amount thereof delivered to treat a target site, upon administration, over a specified period of time, e.g., over more than 1 week, or more than 1 month.

The term "therapeutically effective amount" as used herein refers to an amount of a therapeutic agent which is effective for producing a beneficial or desired clinical result in at least a sub-population of cells in a subject at a reasonable benefit/risk ratio applicable to any medical treatment. For example, a therapeutically effective amount delivered to a target site is sufficient to, directly or indirectly, produce a statistically significant, measurable therapeutic effect as defined herein. By way of example only, the therapeutically effective amount delivered to a target site for treatment is sufficient to reduce at least one symptom or marker associated with the disease or disorder to be treated (e.g., but not limited to, cancer, ocular diseases such as age-related macular degeneration, or neurodegenerative diseases such as Alzheimer's disease) by at least about 10%, at least about 20%, at least about 30%, at least about 40%, at least about 50%, at least about 60% or higher, as compared to absence of the therapeutic agent. In some embodiments, the therapeutically effective amount delivered to a target site for treatment is sufficient to reduce at least one symptom or marker associated with the disease or disorder to be treated (e.g., but not limited to, cancer, ocular diseases such as age-related macular degeneration, or neurodegenerative diseases such as Alzheimer's disease) by at least about 60%, at least about 70%, at least about 80% or higher, as compared to absence of the therapeutic agent. In some embodiments, the therapeutically effective amount delivered to a target site is sufficient to reduce at least one symptom or marker associated with the disease or disorder to be treated (e.g., but not limited to, cancer, ocular diseases such as age-related macular degeneration, or neurodegenerative diseases such as Alzheimer's disease) by at least about 80%, at least about 90%, at least about 95%, at least about 98%, at least about 99%, up to and including 100%, as compared to absence of the therapeutic agent.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy. In some embodiments, the therapeutically effective amount can be in a range between the ED50 and LD50 (a dose of a therapeutic agent at which about 50% of subjects taking it are killed). In some embodiments, the therapeutically effective amount can be in a range between the ED50 (a dose of a therapeutic agent at which a therapeutic effect is detected in at least about 50% of subjects taking it) and the TD50 (a dose at which toxicity occurs at about 50% of the cases). In alternative embodiments, the therapeutically effective amount can be an amount determined based on the current dosage regimen of the same therapeutic agent administered in a non-silk matrix. For example, an upper limit of the therapeutically effective amount can be based on a concentration or an amount of the therapeutic agent delivered to a target site, on the day of administration with the current dosage of the therapeutic agent in a non-silk matrix; while the lower limit of the therapeutically effective amount can be based on a concentration or an amount of the therapeutic agent delivered to a target site, on the day at which a fresh dosage of the therapeutic agent in a non-silk matrix is required.

As used herein, the term "maintain" is used in reference to sustaining a concentration or an amount of a therapeutic agent delivered to a target site at least about or above the therapeutically effective amount over a specified period of time. In some embodiments, the term "maintain" as used herein can refer to keeping the concentration or amount of a therapeutic agent at an essentially constant value over a specified period of time. In some embodiments, the term "maintain" as used herein can refer to keeping the concentration or amount of a therapeutic agent within a range over a specified period of time. For example, the concentration or amount of a therapeutic agent delivered to a target site can be maintained within a range between about the ED50 and about the LD50 or between about the ED50 and about the TD50 over a specified period of time. In such embodiments, the concentration or amount of a therapeutic agent delivered to a target site can vary with time, but is kept within the therapeutically effective amount range for at least 90% of the specified period of time (e.g., at least about 95%, about 98%, about 99%, up to and including 100%, of the specified period of time).

In some embodiments, the therapeutic agent can be present in an amount sufficient to maintain a therapeutically effective amount thereof delivered to a target site, upon administration, over a period of more than 1 week, including, e.g., at least about 2 weeks, at least about 3 weeks, at least about 1 month, at least about 2 months, at least about 3 months, at least about 6 months, at least about 12 months or longer. Such amounts of the therapeutic agent present in a dosage of a silk matrix (e.g., a dosage of silk microspheres) can be generally smaller, e.g., at least about 10% smaller, than the amount of the therapeutic agent present in the current dosage of the treatment regimen (i.e., without silk matrix) required for producing essentially the same therapeutic effect. Accordingly, a dosage of silk matrix (e.g., a dosage of silk microspheres) can comprise the therapeutic agent in an amount which is less than the amount recommended for one dosage of the therapeutic agent. For example, if the recommended dosage of the therapeutic agent is X amount then the silk matrix can comprise a therapeutic agent in an amount of about 0.9X, about 0.8X, about 0.7X, about 0.6X, about 0.5X, about 0.4X, about 0.3X, about 0.2X, about 0.1X or less. Without wishing to be bound by a theory, this can allow administering a lower dosage of the therapeutic agent in a silk matrix to obtain a therapeutic effect which is similar to when a higher dosage is administered without the silk matrix.

In some embodiments, an amount of the therapeutic agent dispersed or encapsulated in a dosage of a silk matrix (e.g., a dosage of silk microspheres) can be more than the amount generally recommended for one dosage of the same therapeutic agent administered for a particular indication. Administration of a therapeutic agent (e.g., bevacizumab) in solution does not generally allow controlled and sustained release. Thus, release rate of a therapeutic agent in solution can generally create a higher initial burst and/or overall faster release kinetics than that of the same amount of the therapeutic agent loaded in silk matrix. However, the silk matrix can act as a depot such that an amount of the therapeutic agent loaded in a silk matrix can be higher than the amount generally recommended for one dosage of the same therapeutic agent and release the therapeutic agent over a period of time, thus providing a longer therapeutic effect with lower frequency of administration. Accordingly, if the recommended dosage of the therapeutic agent is X amount then the silk matrix can encapsulate a therapeutic agent in an amount of about 1.25X, about 1.5X, about 1.75X, about 2X, about 2.5X, about 3X, about 4X, about 5X, about 6X, about 7X, about 8X, about 9X, about 10X or more. Without wishing to be bound by a theory, this can allow administering the therapeutic agent in a silk matrix to obtain a therapeutic effect which is similar to one obtained with multiple administration of the therapeutic agent administered without the silk matrix described herein.

In some embodiments, an amount of the therapeutic agent encapsulated or dispersed in a dosage of the silk matrix (e.g., a dosage of silk microspheres) can be essentially the same amount recommended for one dosage of the therapeutic agent. For example, if the recommended dosage of the therapeutic agent is X amount, then the silk-based composition can comprise about X amount of the therapeutic agent. Without wishing to be bound by a theory, this can allow less frequent administration of the therapeutic agent to obtain a therapeutic effect over a longer period of time.

As used herein, the term "sustained delivery" refers to continual delivery of a therapeutic agent in vivo or in vitro over a period of time following administration. For example, sustained release can occur over a period of at least about 3 days, at least about a week, at least about two weeks, at least about three weeks, at least about four weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months or longer. In some embodiments, the sustained release can occur over a period of more than one month or longer. In some embodiments, the sustained release can occur over a period of at least about three months or longer. In some embodiments, the sustained release can occur over a period of at least about six months or longer. In some embodiments, the sustained release can occur over a period of at least about nine months or longer. In some embodiments, the sustained release can occur over a period of at least about twelve months or longer.

Sustained delivery of the therapeutic agent in vivo can be demonstrated by, for example, the continued therapeutic effect of the agent over time. Alternatively, sustained delivery of the therapeutic agent can be demonstrated by detecting the presence or level of the therapeutic agent in vivo over time. The release rate of a therapeutic agent can be adjusted by a number of factors such as silk matrix composition and/or concentration, porous property of the silk matrix, molecular size of the therapeutic agent, and/or interaction of the therapeutic agent with the silk matrix. For example, if the therapeutic agent has a higher affinity with the silk matrix, the release rate is usually slower than the one with a lower affinity with the silk matrix. Additionally, when a silk matrix has larger pores, the encapsulated therapeutic agent is generally released from the silk matrix faster than from a silk matrix with smaller pores.

In some embodiments, the therapeutic agent can be present in an amount to provide a release profile of the therapeutic agent from the silk matrix such that the amount of the therapeutic agent delivered to a target site is maintained within a therapeutically effective amount range over a period of time. In some embodiments, the therapeutic agent can be present in an amount to provide a release profile of the therapeutic agent with release rates ranging from about 0.01 ng/day to about 1000 mg/day, from about 0.1 ng/day to about 500 mg/day, or from about 1 ng/day to about 250 mg/day over a period of time. Without wishing to be bound by theory, upon administration of a therapeutic agent encapsulated or dispersed in a silk matrix or a composition described herein, there is generally an initial spike in the amount of the therapeutic agent delivered to a target site, and then the release rate of the therapeutic agent from the silk matrix is decreasing over a period of time. Thus, the therapeutic agent can be released initially at a rate as high as mg/day, and later released in a slower rate, e.g., in µg/day or ng/day. Accordingly, in some embodiments, the therapeutic agent can be present in an amount to provide a release profile such that daily release of the therapeutic agent can range from about 1 ng/day to about 1000 mg/day. For example, amount released can be in a range with a lower limit of from 1 to 1000 (e.g., every integer from 1 to 1000) and upper limit of from 1 to 1000 (e.g. every integer from 1 to 1000), wherein the lower and upper limit units can be selected independently from ng/day, g/day, mg/day, or any combinations thereof.

In some embodiments, daily release can vary from about 1 µg/day to about 10 mg/day, from about 0.25 µg/day to about 2.5 mg/day, or from about 0.5 µg/day to about 5 mg/day. In some embodiments, daily release of the therapeutic agent can range from about 100 ng/day to 1 mg/day, for example, or about 500 ng/day to 5 mg/day, or about 100 µg/day.

Stated another way, the therapeutic agent can be released from the silk matrix at a rate such that at least about 5%, including, e.g., at least about 10%, at least about 20%, at least about 30%, at least about 40%, at least about 50%, at least about 60%, at least about 70%, at least about 80%, at least about 90% or more, of the therapeutic agent initially present in the silk matrix can be released over a period of about 3 days, about 1 week, about 10 days, about 20 days, about 1 month, about 2 months, about 3 months, about 4 months, about 5 months, about 6 months, about 7 months, about 8 months, about 9 months, about 10 months, about 11 months, about 12 months or longer. In some embodiments, the therapeutic agent (e.g., bevacizumab) can be released from the silk matrix at a rate such that about 5-30% of the therapeutic agent initially present in the silk matrix can be released over a period of about 3-20 days. In some embodiments, the therapeutic agent (e.g., memantine) can be released from the silk matrix at a rate such that about 40-90% of the therapeutic agent initially present in the silk matrix can be released over a period of about 3-30 days.

The release profiles of the therapeutic agent from a dosage of silk matrix (e.g., a dosage of silk microspheres) or a pharmaceutical composition can be modulated by a number of factors such as amounts and/or molecular size of the therapeutic agents loaded in a silk matrix, porosity of the silk matrix, amounts of silk fibroin in a silk matrix and/or contents of beta-sheet conformation structures in a silk matrix, binding affinity of the therapeutic agent to a silk matrix, and any combinations thereof.

In addition, silk matrix can stabilize the bioactivity of a therapeutic agent under a certain condition, e.g., under an in vivo physiological condition. See, e.g., U.S. Provisional Application No. 61/477,737, the content of which is incorporated herein by reference, for additional details on compositions and methods of stabilization of active agents. Accordingly, in some embodiments, encapsulating a therapeutic agent in a silk matrix can increase the in vivo half-life of the therapeutic agent. For example, in vivo half-life of a therapeutic agent dispersed or encapsulated in a silk matrix can be increased by at least about 5%, at least about 10%, at least about 15%, at least about 20%, at least about 30%, at least about 40%, at least about 50%, at least about 60%, at least about 90%, at least about 1-fold, at least about 1.5-folds relative to the therapeutic agent without the silk matrix. Without wishing to be bound by theory, an increase in in vivo half-life of a therapeutic agent dispersed or encapsulated in a silk matrix can provide a longer therapeutic effect. Stated another way, an increase in in vivo half-life of a therapeutic agent dispersed or encapsulated in a silk matrix can allow loading of a smaller amount of the therapeutic agent for the same duration of therapeutic effect.

In some embodiments, at least one therapeutic agent can be dispersed or encapsulated in the silk matrix. In some embodiments, at least two or more therapeutic agents can be dispersed or encapsulated in the silk matrix. The therapeutic agent can be in any form suitable for a particular method to be used for encapsulation and/or dispersion. For example, the therapeutic agent can be in the form of a solid, liquid, or gel. In some embodiments, the therapeutic agent can be in the form of a powder or a pellet. In some embodiments, the therapeutic agent can be dispersed or encapsulated in a silk solution or matrix before forming the silk matrix. In some embodiments, the therapeutic agent can be dispersed or encapsulated in a silk solution or matrix after forming the silk matrix. For example, the therapeutic agent can be dispersed homogeneously or heterogeneously within the silk matrix, or dispersed in a gradient, e.g., using the carbodiimide-mediated modification method described in the U.S. Patent Application No. US 2007/0212730. In some embodiments, the therapeutic agent can be coated on a surface of the silk matrix, e.g., via diazonium coupling reaction (see, e.g., U.S. Patent Application No. US 2009/0232963), and/or avidin-biotin interaction (see, e.g., International Application No.: WO 2011/011347). In some embodiments, the therapeutic agent can be encapsulated in the silk matrix, e.g., by blending the therapeutic agent into a silk solution before processing into a desired material state, e.g., a hydrogel, or a microsphere or a nanosphere. In some embodiments, the therapeutic agent can be present in a form of a fusion protein with silk protein, e.g., by genetically engineering silk to generate a fusion protein comprising the therapeutic agent.

In some embodiments, the therapeutic agent can be dispersed or encapsulated in a silk matrix after the silk matrix is formed, e.g., by placing the formed silk matrix in a therapeutic agent solution and allowing the therapeutic agent diffuse into the silk matrix over a period of time. In some embodiments, the silk matrix can be optionally hydrated before loading with the therapeutic agent. For example, the silk matrix can be incubated in deionized water until completely hydrated.

Pharmaceutical Compositions and Administration

In yet another aspect, provided herein is a pharmaceutical composition comprising one or a plurality of (e.g., two or more) microspheres described herein, and a pharmaceutically acceptable excipient. In some embodiments, a pharmaceutical composition can comprise a plurality (e.g., two or more) of silk microspheres described herein embedded in a biocompatible polymer as listed herein. In some embodiments, a pharmaceutical composition can comprise a plurality (e.g., two or more) of silk microspheres embedded in a silk hydrogel. The silk hydrogel can be produced by any methods known in the art. Depending on various administration routes, in some embodiments, the pharmaceutical composition can be formulated to be injectable.

The pharmaceutical composition can be formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly or intraocularly (e.g., intravitreous administration); (7) transdermally; (8) transmucosally; or (9) nasally. Additionally, one or more therapeutic agents can be implanted into a patient or injected using a pharmaceutical composition described herein.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of a therapeutic agent and/or imaging agent. Pharmaceutically acceptable carriers include any and all solvents, dispersion media, coatings, antibacterial and antifungal agents, isotonic and absorption delaying agents, and the like which are compatible with the activity of the active agent and are physiologically acceptable to the subject. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

As used herein, the term "administered" refers to the placement of a pharmaceutical composition into a subject by a method or route which results in at least partial localization of the pharmaceutically active agent at a desired site. A pharmaceutical composition described herein can be administered by any appropriate route which results in effective treatment in the subject, i.e. administration results in delivery to a desired location in the subject where at least a portion of the pharmaceutically active agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, intraocular (e.g., intravitreous) and intrasternal injection and infusion.

In some embodiments, a pharmaceutical composition described herein can be implanted in a subject. As used herein, the term "implanted," and grammatically related terms, refers to the positioning of the pharmaceutical composition in a particular locus in the subject, either temporarily, semi-permanently, or permanently. The term does not require a permanent fixation of the pharmaceutical composition in a particular position or location. Exemplary in vivo loci include, but are not limited to site of a wound, trauma or disease.

Method of Use

In another aspect described herein, the silk matrix (e.g., silk microsphere) and/or pharmaceutical composition described herein can be used in various applications, e.g., but not limited to, as a filler to fill a void, e.g., a wound, for medical treatment or for cosmetic applications, or as a carrier to deliver an active agent, e.g., a therapeutic agent, a diagnostic agent, or as a reinforcing material, e.g., in a composite.

In some embodiments, provided herein is a method for imaging at least one cell (including part of a tissue or an organ) in a human or an animal subject by administering a diagnostically effective amount of a pharmaceutical composition comprising a silk microsphere as described herein. For example, the silk microsphere can comprise a contrast agent suitable for the imaging method, e.g., a gadolinium-based contrast agent; a radiocontrast agent such as iodine or barium compounds; iron oxide, iron platinum, manganese or any combinations thereof. After administration of the silk microsphere and/or the pharmaceutical composition described herein, the body of the subject can be examined with a diagnostic device or an imaging system, including, but not limited to, X-ray scanner, magnetic resonance imaging (MRI), and/or computerized axial tomography (CAT scan).

A "diagnostically effective amount" refers to the amount of a silk microsphere or pharmaceutical composition to facilitate a desired diagnostic result. Diagnostics includes testing that is related to the in vitro, ex vivo, or in vivo diagnosis of disease states or biological status (e.g. diabetic, glucose intolerance, iron deficiency, tumor detection, blood flow, etc.) in mammals, for example, but not limited to, humans. The diagnostically effective amount will vary depending upon the specific silk microsphere or composition used, the dosing regimen, timing of administration, the subject and disease condition being diagnosed, the weight and age of the subject, the severity of the disease condition, the manner of administration and the like, all of which can be determined readily by one of ordinary skill in the art.

These imaging methods, as described herein, can be used to diagnose or monitor treatment for conditions such as, but are not limited to, brain tumor; tumors of the chest, abdomen or pelvis; heart problems such as vessel blockage or infarction; diseases of the liver, such as cirrhosis; diagnosis of other abdominal organs, including the bile ducts, gallbladder, and pancreatic ducts; cysts and solid tumors in the kidneys and other parts of the urinary tract; blockages or enlargements of blood vessels, including the aorta, renal arteries, and arteries in the legs; tumors and other abnormalities of the reproductive organs (e.g., uterus, ovaries, testicles, prostate); causes of pelvic pain in women, such as fibroids, endometriosis and adenomyosis; suspected uterine congenital abnormality in women undergoing evaluation for infertility; breast cancer; and breast implants.

In some embodiments, provided herein is also a method for treating a subject with a disease or disorder in a subject by administering to the subject a therapeutically effective amount of a silk microsphere or pharmaceutical composition described herein. In some embodiments, the disease or disorder to be treated include, but not limited to, chronic diseases which can benefit from a treatment involving sustained-release drug delivery, for example, without limitations, cancer, ocular disease such as age-related macular degeneration, neurodegenerative disease such as Alzheimer's disease. Additional exemplary chronic diseases include, but are not limited to, autoimmune disease including autoimmune vasculitis, cartilage damage, chronic inflammatory polyneuropathy (CIDP), cystic fibrosis, diabetes (e.g., insulin diabetes), graft vs. host disease, hemophilia, infection or other disease processes, inflammatory arthritis, inflammatory bowel disease, inflammatory conditions resulting from strain, inflammatory joint disease, lupus, multiple sclerosis, myasthenia gravis, myositis, orthopedic surgery, osteoarthritis, Parkinson's disease, psioriatic arthritis, rheumatoid arthritis, sickle cell anemia, sprain, transplant rejection, trauma, and the like.

In some embodiments, a therapeutically effective amount of a silk microsphere comprising an anti-angiogenic agent (e.g., but not limited to, bevacizumab) or pharmaceutical composition comprising such silk microsphere can be administered to a subject for treatment of cancer. Examples of cancers amenable for the treatment described herein include, but are not limited to, solid tumors including malignancies (e.g., sarcomas and carcinomas (e.g., adenocarcinoma or squamous cell carcinoma)) of the various organ systems, such as those of brain, lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. The cancer can be a carcinoma, a sarcoma, a myeloma, a leukemia, a lymphoma or a mixed type.

In some embodiments, a therapeutically effective amount of a silk microsphere comprising an anti-angiogenic agent (e.g., but not limited to, bevacizumab, ranibizumab, or a mixture thereof) or pharmaceutical composition comprising such silk microsphere can be administered to a subject for treatment of age-related macular degeneration.

In some embodiments, a therapeutically effective amount of a silk microsphere comprising a NMDA receptor antagonist (e.g., but not limited to, memantine) or pharmaceutical composition comprising such silk microsphere can be administered to a subject for treatment of neurodegenerative disease or disorder such as Alzheimer's disease.

In some embodiments of the methods described herein can further comprise selecting a subject diagnosed with or suspected of having a chronic disease or disorder. A subject suffering from a chronic disease or disorder can be selected based on manifestation of at least one symptoms associated with the chronic disease or disorder.

In some embodiments, provided herein is a method for sustained delivery of one or more (e.g., one, two, three, four or more) therapeutic agents to a target site in a subject in need thereof by administering to the subject a pharmaceutical composition comprising a silk matrix or silk microspheres of one or more therapeutic agents. Without wishing to be bound by theory, the therapeutic agent can be released daily from the silk matrix (e.g. silk microsphere) in a therapeutically effective amount as described earlier. Generally, a therapeutically effective amount can vary with the subject's history, age, condition, sex, as well as the severity and type of the medical condition in the subject, and administration of other agents for treatment. Guidance regarding the efficacy and dosage which will deliver a therapeutically effective amount of a compound can be readily obtained from animal models of a condition to be treated by one of skill in the art.

The dosage for the methods of treatment or sustained delivery can be determined by a physician and adjusted, as necessary, to suit observed effects of the treatment. Generally, the therapeutic agents are administered so that the therapeutic agent is given at a dose from 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 g/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. For antibody compounds, one preferred dosage is 0.1 mg/kg of body weight (generally 10 mg/kg to 20 mg/kg).

Without limitations, the method of treatment or sustained delivery described herein can be used for administering, to a subject, a therapeutic agent that requires relatively frequent administration. For example, a therapeutic agent that requires administration at least once a day, at least once every 2 days, at least once every 3 days, at least once every 4 days, at least once every 5 days, at least once every 6 days, at least once every 1 week, at least once every 2 weeks, at least once every 3 weeks, at least once 1 month, at least once every 2 months, at least once every three months, for a period of time, for example over a period of at least one week, at least two weeks, at least three weeks, at least four weeks, at least one month, at least two months, at least three months, at least four months, at least five months, at least six months, at least one years, at least two years or longer.

By "treatment" is meant delaying or preventing the onset of such a disorder or reversing, alleviating, ameliorating, inhibiting, slowing down or stopping the progression, aggravation or deterioration the progression or severity of such a condition. In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

As used herein, a "subject" can mean a human or an animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. In some embodiments, a subject can be of any age, including infants.

In one embodiment, the subject is a mammal. The mammal can be a human, non-human primate, mouse, rat, dog, rabbit, cat, horse, or cow, but are not limited to these examples. Mammals other than humans can be advantageously used as subjects that represent animal models of treatment of a specific disease or disorder. In addition, the methods and compositions described herein can be employed in domesticated animals and/or pets.

Drug Delivery Devices and Kits

Drug delivery devices and kits, e.g., to facilitate administering any embodiments of the compositions and/methods of use are also provided herein. In some embodiments, a drug delivery device can comprise any embodiment of the composition described herein. An drug delivery device can exist in any form, e.g., in some embodiments, the device can be a syringe with an injection needle, e.g., having a gauge of about 25 to about 34 or of about 27 to about 30. Other examples of a drug delivery device that can be used to apply the silk matrix (e.g., silk microsphere) and/or the pharmaceutical composition can include, but are not limited to, a contact lens, a dropper, a microneedle (e.g., a silk microneedle), an implant, and any combinations thereof.

In any embodiment of the drug delivery device, the therapeutic agent dispersed or encapsulate in a silk matrix can vary with desirable administration schedule, and/or release profiles of the therapeutic agent. For example, the therapeutic agent can be present in a silk matrix in an amount sufficient to maintain a therapeutically effective amount thereof delivered to a target site, upon administration, over a period of more than 2 days, including, e.g., more than 3 days, more than 1 week, more than 2 weeks, more than 3 weeks, more than 1 month, more than 2 months, more than 3 months, more than 4 months, more than 5 months, more than 6 months, more than 9 months, more than 12 months or longer. In general, the longer the sustained release of the therapeutic agent to a target site, the less frequently the administration needs to be performed. Amounts or dosages of the therapeutic agent encapsulated or dispersed in a silk matrix as described in any embodiment of the compositions described herein can be applicable to any embodiment of the drug delivery device described herein.

A kit provided herein can generally comprise at least one container containing one or more embodiments of the composition described herein, or at least one drug delivery device in accordance with any embodiments described herein. In some embodiments, e.g., where the composition is not provided or pre-loaded in a delivery device, the kit can further comprise, e.g., a syringe and an injection needle. In some embodiments, the kit can further comprise an anesthetic. In some embodiments, the kit can further an antiseptic agent, e.g., to sterilize an administration site. In some embodiments, the kit can further comprise one or more swabs to apply the antiseptic agent onto the administration site.

Without limitations, methods of sustained delivery described herein, drug delivery devices and/or kits can be applicable for administering, to a subject, a therapeutic agent that requires relatively frequent administration. For example, a therapeutic agent that requires administration at least once every three months, at least once every two months, at least once every week, at least once daily for a period of time, for example over a period of at least one week, at least two weeks, at least three weeks, at least four weeks, at least one month, at least two months, at least three months, at least four months, at least five months, at least six months, at least one years, at least two years or longer.

Embodiments of various aspects described herein can be defined in any of the following numbered paragraphs:

1. A method of preparing a silk microsphere, the method comprising:
   inducing formation of beta-sheet structure of fibroin in a silk solution; and
   inducing formation of a microsphere from the silk solution.
2. The method of paragraph 1, wherein said formation of the beta-sheet structure of fibroin and the microsphere are induced simultaneously.
3. The method of paragraph 1 or 2, wherein said formation of the beta-sheet structure of fibroin in the silk solution is induced by sonication.
4. The method of any of paragraphs 1-3, wherein said formation of the microsphere from the silk solution is induced by atomization of the silk solution.
5. The method of paragraph 2, wherein said formation of the beta-sheet structure of fibroin and the microsphere are induced simultaneously by flowing the silk solution through a flow-through chamber that is ultrasonically activated or an ultrasonic atomizer.
6. The method of paragraph 5, wherein the silk solution is flowed through the flow-through chamber or the ultrasonic atomizer at a flow rate of about 0.001 mL/min to about 5 mL/min.
7. The method of paragraph 6, wherein the silk solution is flowed through the flow-through chamber or the ultrasonic atomizer at the flow rate of about 0.05 mL/min to about 0.3 mL/min.
8. The method of any of paragraphs 3-7, wherein the sonication is performed at a frequency of at least about 10 kHz, or about 20 kHz to about 40 kHz.
9. The method of any of paragraphs 3-8, wherein the sonication power output ranges from about 1 watt to about 50 watts, or from about 2 watts to about 20 watts.
10. The method of any of paragraphs 1-9, further comprising freezing the silk microsphere.
11. The method of paragraph 10, wherein the silk microsphere can be frozen by exposing the silk microsphere to a sub-zero temperature.
12. The method of paragraph 10 or 11, wherein the silk microsphere is exposed to the sub-zero temperature by collecting the silk microsphere in a container cooled by a cooling agent.
13. The method of any of paragraphs 1-12, further comprising subjecting the silk microsphere to lyophilization.
14. The method of any of paragraphs 1-13, wherein the silk microsphere has a porosity of at least about 30%.
15. The method of any of paragraphs 1-14, wherein the silk microsphere has a pore size of about 1 nm to about 500 µm, or 10 nm to about 50 µm.
16. The method of any of paragraphs 1-15, wherein the silk solution comprises silk fibroin at a concentration of about 1% (w/v) to about 30% (w/v).
17. The method of paragraph 16, wherein the silk solution comprises silk fibroin at a concentration of about 5% (w/v).
18. The method of any of paragraphs 1-17, wherein the silk microsphere comprises an active agent.
19. The method of paragraph 18, wherein the active agent includes a temperature-sensitive active agent.
20. The method of paragraph 18 or 19, wherein the active agent is a therapeutic agent.
21. The method of paragraph 20, wherein the therapeutic agent is selected from the group consisting of small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; antibodies and antigen binding fragments thereof; an extract made from biological materials such as bacteria, plants, fungi, or animal cells; animal tissues; naturally occurring or synthetic compositions; and any combinations thereof.
22. The method of paragraph 20 or 21, wherein the therapeutic agent includes bevacizumab, memantine, or a combination thereof.
23. The method of any of paragraphs 18-22, wherein the active agent is present in the silk microsphere in an amount of about 0.1% (w/w) to about 50% (w/w).
24. The method of paragraph 23, wherein the active agent is present in the silk microsphere in an amount of about 1% (w/w) to about 30% (w/w).
25. The method of any of paragraphs 18-24, wherein the active agent is present in the silk solution.
26. The method of any of paragraphs 1-25, wherein the silk microsphere comprises silk in an amount of about 30% (w/w) to about 100% (w/w), of the total weight of the microsphere.
27. The method of any of paragraphs 1-26, wherein the silk solution further comprises an additive.
28. The method of paragraph 27, wherein a weight ratio of the additive to silk in the silk solution is about 1:100 to about 100:1.
29. The method of paragraph 27 or 28, wherein the weight ratio of the additive to silk in the silk solution is about 1:10 to about 10:1.
30. The method of any of paragraphs 27-29, wherein the additive is selected from the group consisting of a biopolymer, a porogen, a magnetic particle, a plasticizer, a detection label, and any combinations thereof.
31. The method of any of paragraphs 27-30, wherein the additive is a plasticizer.
32. The method of paragraph 30 or 31, wherein the plasticizer induces formation of beta-sheet crystalline structure of fibroin in the silk.
33. The method of any of paragraphs 30-32, wherein the plasticizer is selected from the group consisting of glycerol, polyvinyl alcohol, collagen, gelatin, alginate, chitosan, hyaluronic acid, polyethylene glycol, polyethylene oxide, and any combinations thereof.
34. The method of any of paragraphs 1-33, further comprising subjecting the silk microsphere to a post-treatment.
35. The method of paragraph 34, wherein the post-treatment further induces formation of beta-sheet crystalline structure of fibroin in the silk microsphere.
36. The method of any of paragraphs 34-35, wherein the post-treatment is selected from the group consisting of alcohol immersion, water vapor annealing, heat annealing, and any combinations thereof.
37. The method of any of paragraphs 34-36, wherein the silk microsphere prior to the post-treatment has a water solubility of less than 50%.
38. The method of any of paragraphs 34-37, wherein the silk microsphere prior to the post-treatment has a water solubility of less than 30%.
39. The method of any of paragraphs 1-38, wherein the silk microsphere has a size of about 10 µm to about 1000 µm.

40. The method of any of paragraphs 1-39, wherein the silk microsphere has a size of about 50 μm to about 100 μm.
41. The method of any of paragraphs 4-40, wherein the atomization comprises using a spray nozzle system of a droplet generator.
42. The method of any of paragraphs 4-41, wherein the atomization comprises syringe extrusion, coaxial air flow method, mechanical disturbance method, electrostatic force method, or electrostatic bead generator method.
43. The method of any of paragraphs 4-42, wherein the atomization comprises spraying the silk solution through a nozzle of an air driven droplet generating encapsulation unit.
44. The method of any of paragraphs 1-43, wherein a shape or a size of the silk microsphere is varied by varying one or more parameters selected from the group consisting of nozzle diameter; flow rate of the spray; pressure of the spray; distance of the container collecting the silk microsphere from the nozzle; concentration of the silk solution; power of sonication waves; sonication treatment time; and any combinations thereof.
45. A silk microsphere prepared using the method of any of paragraphs 1-44.
46. The silk microsphere of paragraph 45, wherein the silk microsphere releases at least about 5% of the active agent loaded therein over a period of at least about 10 days.
47. A pharmaceutical composition comprising the silk microsphere of any of paragraphs 45-46 and a pharmaceutically acceptable excipient.
48. The composition of paragraph 47, wherein the composition is formulated to be injectable.
49. A method of sustained delivery in vivo of a therapeutic agent comprising administering the pharmaceutical composition of any of paragraphs 47-48 to a subject in need thereof.
50. A composition comprising a silk microsphere having a size of about 10 μm to about 2000 μm.
51. The composition of paragraph 50, wherein the size of the silk microsphere is about 30 μm to about 1000 μm.
52. The composition of paragraph 50 or 51, wherein the silk microsphere is water-insoluble.
53. The composition of any of paragraphs 50-52, wherein the water-insoluble silk microsphere has a beta sheet crystalline content of at least about 50% or higher.
54. The composition of any of paragraphs 50-53, wherein the silk microsphere further comprises an active agent.
55. The composition of paragraph 54, wherein the active agent is solvent-sensitive and/or temperature-sensitive active agent.
56. The composition of any of paragraphs 50-55, wherein the active agent is selected from the group consisting of small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; antibodies and antigen binding fragments thereof; therapeutic agents; an extract made from biological materials such as bacteria, plants, fungi, or animal cells; animal tissues; naturally occurring or synthetic compositions; and any combinations thereof.
57. The composition of paragraph 56, wherein the therapeutic agent comprises bevacizumab, memantine, or a combination thereof.
58. The composition of any of paragraphs 54-57, wherein the silk microsphere comprising the active agent has a release profile of about 1% release to about 50% release of the total loading of the active agent over a period of 5 days.
59. The composition of paragraph 58, wherein the release profile comprises a sustained release.
60. The composition of paragraph 59, wherein the release profile further comprises an immediate release.
61. The composition of any of paragraphs 50-60, wherein the active agent is present in the silk microsphere in an amount of about 0.1% (w/w) to about 50% (w/w).
62. The composition of any of paragraphs 50-61, wherein the silk microsphere comprises silk fibroin in an amount of about 10% (w/w) to about 100% (w/w), of the total weight of the microsphere.
63. The composition of any of paragraphs 50-62, wherein the silk microsphere further comprises an additive.
64. The composition of paragraph 63, wherein a weight ratio of the additive to silk fibroin in the silk microsphere is about 1:100 to about 100:1.
65. The composition of paragraph 63 or 64, wherein the additive is selected from the group consisting of a biopolymer, a porogen, a magnetic particle, a plasticizer, a detection label, and any combinations thereof.
66. The composition of paragraph 65, wherein the additive comprises a plasticizer.
67. The composition of paragraph 66, wherein the plasticizer induces formation of beta-sheet crystalline structure of fibroin in the silk.
68. The composition of paragraph 66 or 67, wherein the plasticizer is selected from the group consisting of glycerol, polyvinyl alcohol, collagen, gelatin, alginate, chitosan, hyaluronic acid, polyethylene glycol, polyethylene oxide, and any combinations thereof.
69. The composition of paragraph 68, wherein the additive comprises glycerol.
70. The composition of paragraph 69, wherein the ratio of glycerol to silk fibroin the silk microsphere ranges from about 1:10 to about 10:1.
71. The composition of any of paragraphs 50-70, wherein the composition is injectable.
72. The composition of any of paragraphs 50-71, wherein the composition is a pharmaceutical composition.
73. The composition of paragraph 72, further comprises a pharmaceutically acceptable excipient.
74. The composition of paragraph 72 or 73, wherein the pharmaceutical composition is in a form of a tablet, a capsule, a lozenge, powder, paste, granules, a liquid, a solution, gel, or any combinations thereof.
75. The composition of any of paragraphs 50-74, wherein the silk microsphere is porous.

Some Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

The term "nucleic acids" used herein refers to polynucleotides such as deoxyribonucleic acid (DNA), and, where appropriate, ribonucleic acid (RNA), polymers thereof in either single- or double-stranded form. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985), and Rossolini, et al., Mol. Cell. Probes 8:91-98 (1994)). The term "nucleic acid" should also be understood to include, as equivalents, derivatives, variants and analogs of either RNA or DNA made from nucleotide analogs, and, single (sense or antisense) and double-stranded polynucleotides.

The term "short interfering RNA" (siRNA), also referred to herein as "small interfering RNA" is defined as an agent which functions to inhibit expression of a target gene, e.g., by RNAi. An siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense 60 strand and/or the antisense strand. The term "siRNA" includes duplexes of two separate strands, as well as single strands that can form hairpin structures comprising a duplex region.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

The term "enzymes" as used here refers to a protein molecule that catalyzes chemical reactions of other substances without it being destroyed or substantially altered upon completion of the reactions. The term can include naturally occurring enzymes and bioengineered enzymes or mixtures thereof. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases.

The term "vaccines" as used herein refers to any preparation of killed microorganisms, live attenuated organisms, subunit antigens, toxoid antigens, conjugate antigens or other type of antigenic molecule that when introduced into a subjects body produces immunity to a specific disease by causing the activation of the immune system, antibody formation, and/or creating of a T-cell and/or B-cell response. Generally vaccines against microorganisms are directed toward at least part of a virus, bacteria, parasite, mycoplasma, or other infectious agent.

As used herein, the term "aptamers" means a single-stranded, partially single-stranded, partially double-stranded or double-stranded nucleotide sequence capable of specifically recognizing a selected non-oligonucleotide molecule or group of molecules. In some embodiments, the aptamer recognizes the non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. Methods for selecting aptamers for binding to a molecule are widely known in the art and easily accessible to one of ordinary skill in the art.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as portions of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

The term "antibiotics" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillins, cephalosporins, penems, carbapenems, monobactams, aminoglycosides, sulfonamides, macrolides, tetracyclines, lincosides, quinolones, chloramphenicol, vancomycin, metronidazole, rifampin, isoniazid, spectinomycin, trimethoprim, sulfamethoxazole, and the like.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

The term "immunogen" refers to any substance, e.g., vaccines, capable of eliciting an immune response in an organism. An "immunogen" is capable of inducing an immunological response against itself on administration to a subject. The term "immunological" as used herein with respect to an immunological response, refers to the development of a humoral (antibody mediated) and/or a cellular (mediated by antigen-specific T cells or their secretion products) response directed against an immunogen in a recipient subject. Such a response can be an active response induced by administration of an immunogen or immunogenic peptide to a subject or a passive response induced by administration of antibody or primed T-cells that are directed towards the immunogen. A cellular immune response is elicited by the presentation of polypeptide epitopes in association with Class I or Class II MHC molecules to activate antigen-specific CD4+ T helper cells and/or CD8+ cytotoxic T cells. Such a response can also involve activation of monocytes, macrophages, NK cells, basophils, dendritic cells, astrocytes, microglia cells, eosinophils or other components of innate immunity.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Exemplary Materials and Methods

Materials:

Degummed silk fibers were purchased from Suho Biomaterials Technology (Suzhou, China). Bevacizumab (AVASTIN®, Genentech, South San Francisco, Calif.) was purchased from CuraScript Inc. (Orlando, Fl). Memantine hydrochloride and all other chemicals were purchased from Sigma-Aldrich (St. Louis, Mo.).

Silk Fibroin Protein Purification.

To obtain silk fibroin solution from degummed silk fibers, multiple purification steps including lithium bromide dissolution, dialysis and centrifugation were performed. Briefly, 5 g of degummed fibers were weighed and added to a container, e.g., a glass beaker, containing 20 ml of freshly prepared 9.3 M lithium bromide solution. The final concentration of silk was approximately 20% (w/v). The mixture was then heated until the silk fibers were completely dissolved. For example, the container was covered with an aluminum foil and placed in an oven at 60° C. for 4 hours until the silk fibers were completely dissolved. The solution was dialyzed against ultrapure water (e.g., with an electrical resistivity of about 18.2 MΩcm), for example, using Slide-a-Lyzer dialysis cassettes (MWCO 3,500, Pierce/Thermo Scientific, Rockford, Ill.) for 48 hours, to remove the lithium bromide salt. The dialyzed solution was centrifuged twice at 8,700 rpm and 4° C. for about 20 minutes using 50-ml conical tubes in an Eppendorf 5804R centrifuge. The final concentration of silk fibroin aqueous solution was approximately 8% (w/v), as measured by drying a known volume of solution at 60° C. overnight and weighing the residual solid. The 8% silk stock solution was stored at 4° C. and diluted with ultrapure water before use.

Spray-Crystallize-Freeze-Drying (SCFD) Set-Up.

While an exemplary SCFD set-up was described in the Examples, any other modifications within one of skill in the art are still within the scope described herein. In one embodiment, a SONIFIER® cell disruptor (Branson, Danbury, Conn.) equipped with a flow-through horn and a syringe pump (KDS230, KD Scientific, Holliston, Mass.) were used in the preparation to atomize the silk solution and to induce formation of beta-sheet crystalline structure in silk fibroin simultaneously. Silk solution was injected into the flow-through horn via the syringe pump at desired flow rates and sprayed through the horn directly into a fast-freeze container (e.g., a 600-ml fast-freeze flask, which can be obtained from Labconco Corp., Kansas City, Mo.). The flask was kept floating in liquid nitrogen (FIG. 1), while the distance between the tip of the horn and the bottom of the flask was adjusted to ensure both immediate freezing of the spray and spray homogeneity. After spraying, the flask was immediately loaded into a Virtis Genesis lyophilizer (SP Scientific, Warminster, Pa.) and lyophilized overnight.

Preparation of SCFD Microspheres.

The composition of the silk solution, the flow rate (controlled via the syringe pump) and the sonication power output were varied for preparing different SCFD microspheres. To facilitate comparison among different SCFD microspheres, the solution volume was kept constant at 5 mL for all batches, while other variables such as amounts of silk, amounts of an additive (e.g., glycerol to decrease solubility of silk microspheres), flow rates, and sonication power were adjusted. Some exemplary values of those variables for production of silk microspheres are listed in Table 1.

TABLE 1

Exemplary parameters for production of silk microspheres described herein (based on a ~5-mL solution volume)

| | |
|---|---|
| Amount of silk | ~50-~400 mg |
| Amount of glycerol | ~0-~170 mg |
| Flow rate | ~0.1-~1.0 mL/min |
| Sonication power | ~25-~55% amplitude |

Microsphere Characterization (Size, Morphology and Solubility).

The size and surface morphology of SCFD microspheres were assessed in both freeze-dried (powder) form and after suspension of dried powder in ultrapure water, e.g., using an inverted optical microscope (Carl Zeiss, Jena, Germany) and a Scanning Electron Microscope (SEM, JSM 840A, JEOL Peabody, Mass.). For SCFD microsphere assessment using an optical microscope, the dried powder or approximately 20 μL of a water suspension of microspheres was directly added on top of a glass slide. For SEM, the dried powder was applied directly onto an SEM stub covered with a conductive tape (JEOL Peabody, Mass.), while the water suspension of microspheres was loaded onto an SEM stub with a conductive tape and dried overnight at ambient temperature. The samples were sputter-coated with approximately 20 nm of gold prior to SEM analysis.

The solubility of SCFD microspheres can be estimated by any art-recognized method. In one embodiment, the solubility of SCFD microspheres was estimated, e.g., using the following protocol. First, an aqueous microsphere suspension (1% w/v) was centrifuged at 15000 rpm for about 10 minutes (e.g., using an Eppendorf 5424 microcentrifuge) after incubation at 37° C. for about 2 hours with agitation (e.g., placing the suspension on a shaker). After removal of the supernatant, the remaining microspheres were dried at 60° C. overnight and subsequently weighed to obtain the weight of the dried pellet. The microsphere solubility was estimated from the ratio of the difference between the initial microsphere mass and the dried pellet mass to the initial microsphere mass.

Preparation of Drug-Loaded SCFD Spheres.

For therapeutic drug-loaded SCFD spheres (e.g., bevacizumab-loaded SCFD spheres: A-sphere; or memantine hydrochloride-loaded SCFD spheres: M-sphere), the drug solution was mixed with silk and glycerol solutions prior to spraying. The total solution volume was kept constant at 5 mL, while the mixing ratio of different components (e.g., drug, silk and glycerol) and the sonication power were varied, as shown in Table 2.

TABLE 2

Exemplary parameters for preparation of drug-loaded silk-glycerol microspheres

| Batch | Amount of drug (mg) | Amount of silk (mg) | Amount of glycerol (mg) | Sonication power (% amplitude) | Flow rate (ml/min) |
|---|---|---|---|---|---|
| M-sphere 1 | 62.5 | 250.0 | 0.0 | 25 | 0.17 |
| M-sphere 2 | 62.5 | 250.0 | 45.0 | 25 | 0.17 |
| M-sphere 3 | 62.5 | 250.0 | 83.5 | 25 | 0.17 |
| A-sphere 1 | 10.0 | 250.0 | 0.0 | 25 | 0.17 |
| A-sphere 2 | 10.0 | 250.0 | 45.0 | 25 | 0.17 |
| A-sphere 3 | 10.0 | 250.0 | 83.5 | 25 | 0.17 |
| A-sphere 4 | 10.0 | 250.0 | 83.5 | 20 | 0.17 |
| A-sphere 5 | 10.0 | 62.5 | 21.0 | 25 | 0.17 |
| A-sphere 6 | 10.0 | 30.0 | 10.0 | 25 | 0.17 |

Drug Release from SCFD Microspheres.

Silk microspheres were stored in sealed glass vials at 4° C. prior to release studies. Before use, approximately 10 mg of powder was weighed and added to a 15-ml plastic tube, to which 4 ml of PBS buffer, pH 7.4 containing 0.02% (w/v) sodium azide was added. The microsphere suspension was then incubated at 37° C. At desired time points, the tubes containing silk microspheres were centrifuged at 10,000 rpm for about 10 min (e.g., using Eppendorf 5804R centrifuge), and the supernatants were collected and stored at 4° C. for analysis. The microsphere pellets were resuspended with 4 ml of PBS/sodium azide buffer, pH 7.4 and incubated until the next time point. Memantine concentration in the release medium was determined using a modification of the method previously described in Suckow R F et al. "Sensitive and selective liquid chromatographic assay of memantine in plasma with fluorescence detection after pre-column derivatization." J Chromatogr B Biomed Sci Appl 1999; 729:217-224. Some modifications include a fluorescence labeling reaction with dansyl chloride and High Pressure Liquid Chromatography (HPLC) using an Agilent 1200 series HPLC (Agilent, Santa Clara, Calif.) instrument equipped with a reverse phase column (Agilent Eclipse plus C-18 column, 4.6 mm I.D.×75 mm L). Bevacizumab concentration was analyzed using the same HPLC system equipped with an Agilent Bio SEC-3 column (300 angstrom pore size, 4.6 mm I.D.×300 mm L).

Example 2: Role of Sonication in Silk SCFD Microsphere Preparation

Sonication has been used to induce silk fibroin gelation, e.g., as reported in Wang X et al. "Sonication-induced gelation of silk fibroin for cell encapsulation." Biomaterials 2008; 29:1054-64. The time for silk gelation was dependent on silk solution concentration, sonication power output, and sonication duration. Id. However, the Wang X et al. reference does not describe the use of sonication to produce silk microspheres. Presented herein is one embodiment of the methods for preparing a silk microsphere, in which a sonicator (Branson SONIFIER® cell disruptor) equipped with a flow-through horn was utilized to allow silk solution to be continuously sonicated as it passed through the inner channel of the horn, while concomitantly being atomized into a fine spray at the nozzle (e.g., tip) of the horn (FIG. 1). The atomized spray was collected as frozen particles in a flask that was at least partially surrounded by liquid nitrogen, and the frozen particles were subsequently lyophilized into dry particles.

Without wishing to be bound by theory, dry silk particles after lyophilization can gain certain amount of beta-sheet crystalline structure due to sonication, which can result in formation of water-insoluble particles. Accordingly, further solvent treatment to induce crystallization can be unnecessary. It has been previously reported that silk microspheres that were fabricated by a spray-drying process gained a certain amount of beta-sheet structure either due to the high temperature in the spray-dryer (Hino T. et al. "Silk microspheres prepared by spray-drying of an aqueous system." Pharm Pharmacol Commun 2000; 6:335-339; Yeo J H. et al. "Simple preparation and characteristics of silk fibroin microsphere." Eur Polym J 2003; 39:1195-1199) or due to a post-lyophilization treatment using methanol or water vapor (Wenk E. et al. "Silk fibroin spheres as a platform for controlled drug delivery." J Control Release 2008; 132:26-34). However, unlike the methods described herein, these previous reports show that heat and/or post-treatment with methanol or water vapor are required to induce sufficient amounts of beta-sheet structure of silk fibroin present in silk microspheres such that the silk microspheres have a low solubility or become insoluble in water.

Without wishing to be bound by theory, the increase in beta-sheet content in silk fibroin resulted in the preservation of shape and size of microspheres in water. The water solubility of SCFD microparticles was estimated by comparing the particle size and morphology in dry and wet states using both optical and scanning electron microscopy. The weight loss of silk material due to dissolution in water was further quantified. The results of microscopy and dissolution tests were summarized in Table 3.

TABLE 3

Exemplary parameters for preparation of silk microspheres

| | Amount of silk (mg) | Flow rate (ml/min) | Sonication power (% amplitude) | Morphology/ Polydispersity | Morphology after hydration* | Solubility (%) |
|---|---|---|---|---|---|---|
| 1 | 50 | 0.1 | 25 | Fibers/ Aggregates | N.T. | N.T. |
| 2 | 250 | 0.1 | 25 | Spherical/ 50-100 μm | Dissolved | 91 ± 4 |

TABLE 3-continued

Exemplary parameters for preparation of silk microspheres

| | Amount of silk (mg) | Flow rate (ml/min) | Sonication power (% amplitude) | Morphology/ Polydispersity | Morphology after hydration* | Solubility (%) |
|---|---|---|---|---|---|---|
| 3 | 400 | 0.1 | 25 | Spherical/ 50-100 μm | Dissolved | 87 ± 5 |
| 4 | 250 | 0.5 | 25 | Spherical/ 100-500 μm | Dissolved | 93 ± 3 |
| 5 | 250 | 1.0 | 25 | Spherical/ 100-800 μm | Dissolved | 90 ± 3 |
| 6 | 250 | 0.5 | 35 | Spherical/ 100-800 μm | Deformed** | 21 ± 9 |
| 7 | 250 | 0.1 | 35 | Spherical/ 100-500 μm | Deformed** | 9 ± 2 |
| 8 | 250 | 0.5 | 45 | Aggregates/ 100-800 μm/ | Deformed** | 8 ± 2 |
| 9 | 250 | 0.5 | 55 | Fibers/ Aggregates | N.T. | N.T. |

N.T. = not tested
*Determined via optical microscopy.
**Microspheres lost their spherical shape and formed aggregated clumps that floated in water.

Figure 2A:
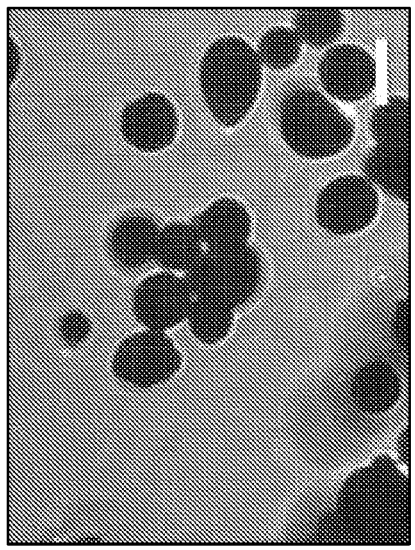
FIGS. 2A-2D are optical microscope images of silk SCFD spheres in accordance with one or more embodiments described herein.
Figure 2B:
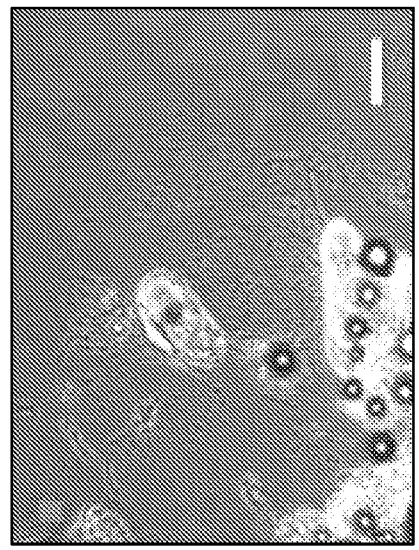
Figure 2C:
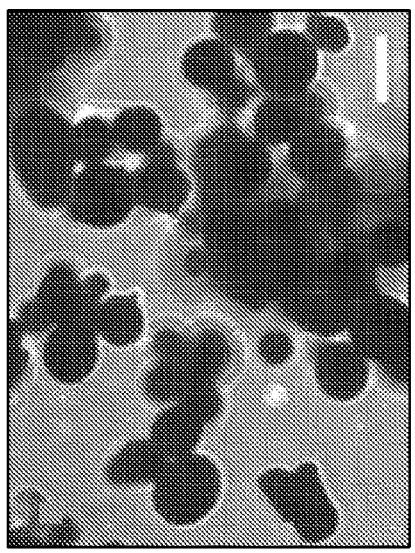
Figure 2D:
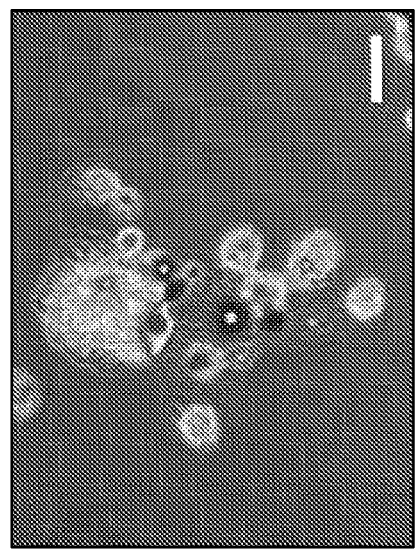

As shown in Table 3, silk microspheres were generally obtained at higher silk solution concentrations, e.g., ~5-8% (w/v), but not at lower concentrations (e.g. ~1% (w/v)). With too high silk concentration, however, the silk solution was more prone to faster gelation, which could cause clogging in the flow-through horn. Therefore, ~5% (w/v) silk concentration was used in the Examples described herein. In addition to silk concentrations, the flow rates and/or sonication power output can have significant influence on microsphere microstructure and/or water solubility. In some embodiments, silk microspheres prepared at a flow rate higher than 0.1 ml/min and a sonication power output lower than 35% amplitude were highly soluble in water, likely due to their low beta-sheet contents. These microspheres collapsed and eventually deformed into aggregated fibers within a few minutes upon hydration, with a high solubility in water of above 80% by mass (FIGS. 2C and 2D, Table 3 above). In some embodiments, as shown in Table 3, silk microspheres prepared at a sonication power output higher than 35% amplitude had a lower yield, likely due to gelation during sonication, but had significantly lower solubility (~8-20% by mass), indicating that a significant amount of beta-sheet crystalline structure could have formed under these conditions. However, upon hydration, the silk microspheres formed aggregated, low density clumps that floated in water. In order to obtain a non-aggregated suspension of silk microspheres with low water solubility, in one embodiment, at least one additive capable of enhancing silk beta-sheet crystallinity can be added into the silk solution prior to flow sonication (Lu S. et al. "Insoluble and flexible silk films containing glycerol." Biomacromolecules 2010; 11:143-150).

Example 3. Role of Beta-Sheet Structure-Inducing Additives in Silk SCFD Microsphere Preparation It was next sought to determine the effects of various beta-sheet structure-inducing additives on solubility of silk SCFD microspheres. Poly(vinyl alcohol) (PVA) has been previously used to obtain water-insoluble silk nano-/microspheres via phase separation (See, e.g., Wang X. et al. "Silk nanospheres and microspheres from silk/PVA blend films for drug delivery." Biomaterials 2010; 31:1025-1035). However, poly(vinyl alcohol) (PVA) did not significantly affect the solubility of the microspheres produced by the methods described herein. Glycerol is an additive previously used to produce insoluble and flexible silk films (Lu S. et al. "Insoluble and flexible silk films containing glycerol." Biomacromolecules 2010; 11:143-150). The inventors have demonstrated that, unlike PVA, glycerol can decrease the solubility of silk microspheres produced by the methods described herein, while preserving the non-aggregated spherical morphology in water. Table 4 shows some exemplary parameters (e.g., but not limited to, flow rate, sonication power, silk to glycerol ratio, and silk and glycerol concentrations) varied to optimize processing conditions for microsphere production.

TABLE 4

Exemplary parameters for preparation of silk-glycerol microspheres

| | Amount of silk (mg) | Amount of glycerol (mg) | Flow rate (ml/min) | Sonication power (% amplitude) | Morphology/ Polydispersity | Morphology after hydration* | Solubility (%) |
|---|---|---|---|---|---|---|---|
| 1 | 250 | 83.50 | 0.10 | 25 | Spherical/ 30-100 μm | Aggregated/ Partially dissolved | 23 ± 6 |
| 2 | 250 | 83.50 | 0.17 | 25 | Spherical/ 50-100 μm | Maintained original shape | 24 ± 6 |
| 3 | 250 | 83.50 | 0.25 | 25 | Spherical/ 50-100 μm | Aggregated/ Partially dissolved | 25 ± 3* |

TABLE 4-continued

Exemplary parameters for preparation of silk-glycerol microspheres

| | Amount of silk (mg) | Amount of glycerol (mg) | Flow rate (ml/min) | Sonication power (% amplitude) | Morphology/ Polydispersity | Morphology after hydration* | Solubility (%) |
|---|---|---|---|---|---|---|---|
| 4 | 250 | 83.50 | 0.17 | 15 | Fibers & aggregates | N.T. | N.T. |
| 5 | 250 | 83.50 | 0.17 | 40 | Spherical/ 500-800 μm | Maintained original shape | 28 ± 1 |
| 6 | 250 | 41.75 | 0.17 | 25 | Spherical/ 100-800 μm | Partially dissolved | 53 ± 5 |
| 7 | 250 | 167.00 | 0.17 | 25 | Non-spherical/<100 μm | Partially dissolved | 52 ± 2 |
| 9 | 125 | 41.75 | 0.17 | 25 | Non-spherical/ 50-100 μm | Maintained original shape | 24 ± 4 |
| 10 | 400 | 134.00 | 0.17 | 25 | Spherical/ 100-500 μm | Maintained original shape** | 22 ± 2 |

N.T. = not analyzed
*Determined by optical microscope.
**Silk gelled in the flow-through horn during sonication.

Figure 3B:
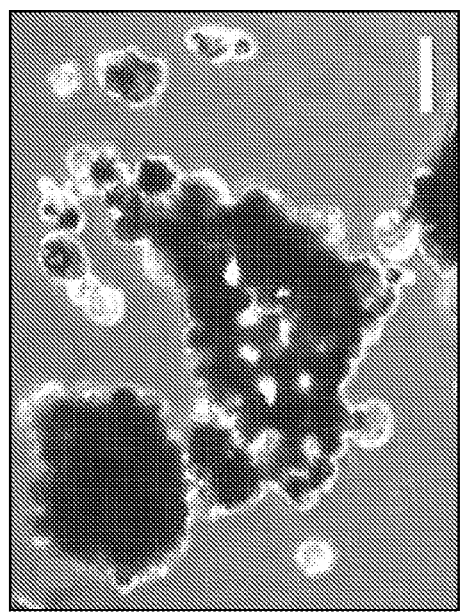
FIGS. 3A-3B are optical microscope images of silk/glycerol SCFD microspheres in accordance with one or more embodiments described herein.
Figure 3A:
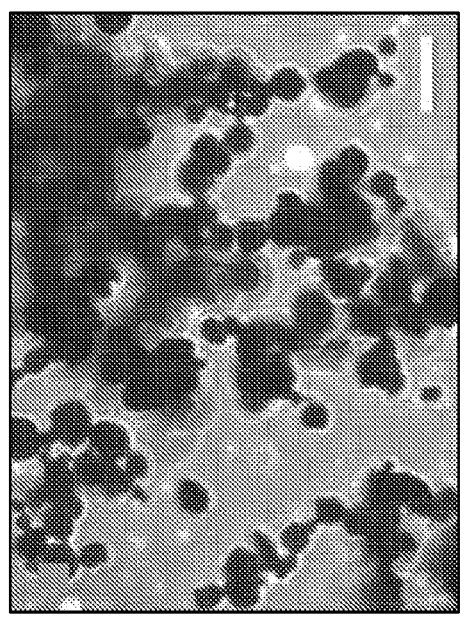
Figure 4A:
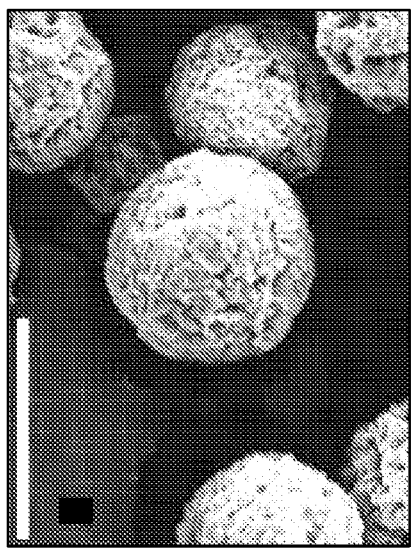
FIGS. 4A-4D are scanning electron microscopy (SEM) images of silk/glycerol SCFD microspheres with or without memantine in accordance with one or more embodiments described herein.
Figure 4B:
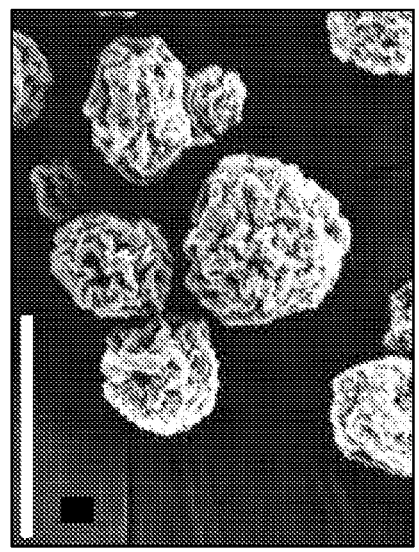
Figure 4C:
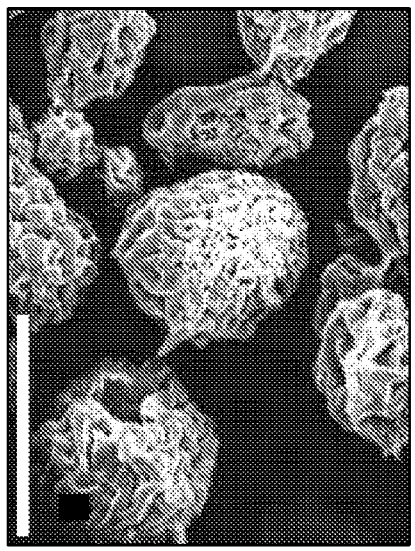
Figure 4D:
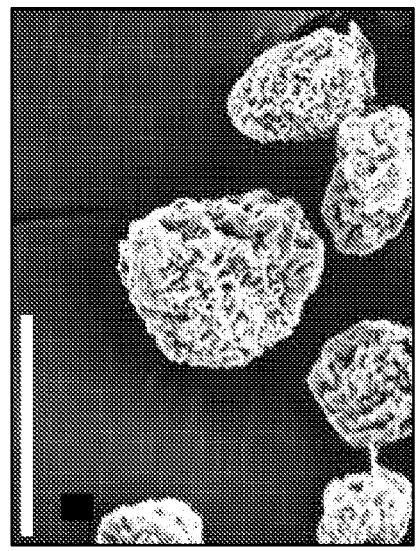

Compared to silk alone (Table 3), the silk/glycerol mixed solution (Table 4) was more sensitive to sonication power output and/or flow rate changes. In some embodiments, a flow rate of about 0.17 ml/min and a sonication amplitude of about 25% amplitude were determined to be the optimum processing conditions, in which a predominantly microspherical morphology with less than 30% water solubility was produced, indicating a relatively high beta-sheet content (Table 4, FIGS. 3A-3B). From previous reports on silk-glycerol blend films (Id.), almost all glycerol was dissolved in water in about one hour after film hydration, during which the overall silk beta-sheet content increased from about 10% to above 50%, as determined by Fourier Transform Infrared (FTIR) spectroscopy. As a result, these films not only preserved their original dimensions but also had an improved mechanical strength. Id. In the Example described herein, without wishing to be bound by theory, the 30% mass loss upon hydration of microspheres could be attributed mainly to dissolution of glycerol in water. Accordingly, in some embodiments, the silk microspheres can have an effective solubility of higher than 90%. In other embodiments, there can be an overall beta-sheet crystalline content of over 50% in the silk/glycerol microspheres. Without wishing to be by theory, higher flow rates (>~0.17 ml/min) and/or lower sonication amplitudes (<25%) resulted either in the lack of a spray or high water solubility of microspheres, while lower flow rates and/or higher sonication amplitudes generally resulted in premature silk gelation, e.g., in a sonifier. In the previous reports on silk/glycerol blend films, the weight ratio of glycerol to silk was reported to be over 1/3 in order to prepare water-insoluble films. Id. However, those previous reports do not indicate the weight ratio of glycerol to silk in microspheres. It was determined herein that a ratio of glycerol to silk at about 1/3 can produce a microspherical morphology and low water solubility. On the other hand, ratios of glycerol to silk much higher than about 1/3 can cause premature silk/glycerol gelation in the sonifier and/or formation of non-spherical particles. However, in particular embodiments, water insoluble microsphere preparation was not possible when ratios of glycerol to silk was below about 1/3 at a flow rate of about 0.17 ml/min and a sonication amplitude of about 25%. Therefore, in one embodiment, ~5% silk/~1.67% glycerol (w/v) is used to encapsulate a drug for drug delivery applications. In such embodiments, the microspheres can have sizes ranging from about 50 μm to about 100 μm with high nano-/microporosity, as visualized via optical and scanning electron microscopy (FIGS. 4A-4D).

Example 4. Exemplary Silk SCFD Microspheres for Drug Delivery

Memantine-Silk SCFD Microspheres.

Figure 5:
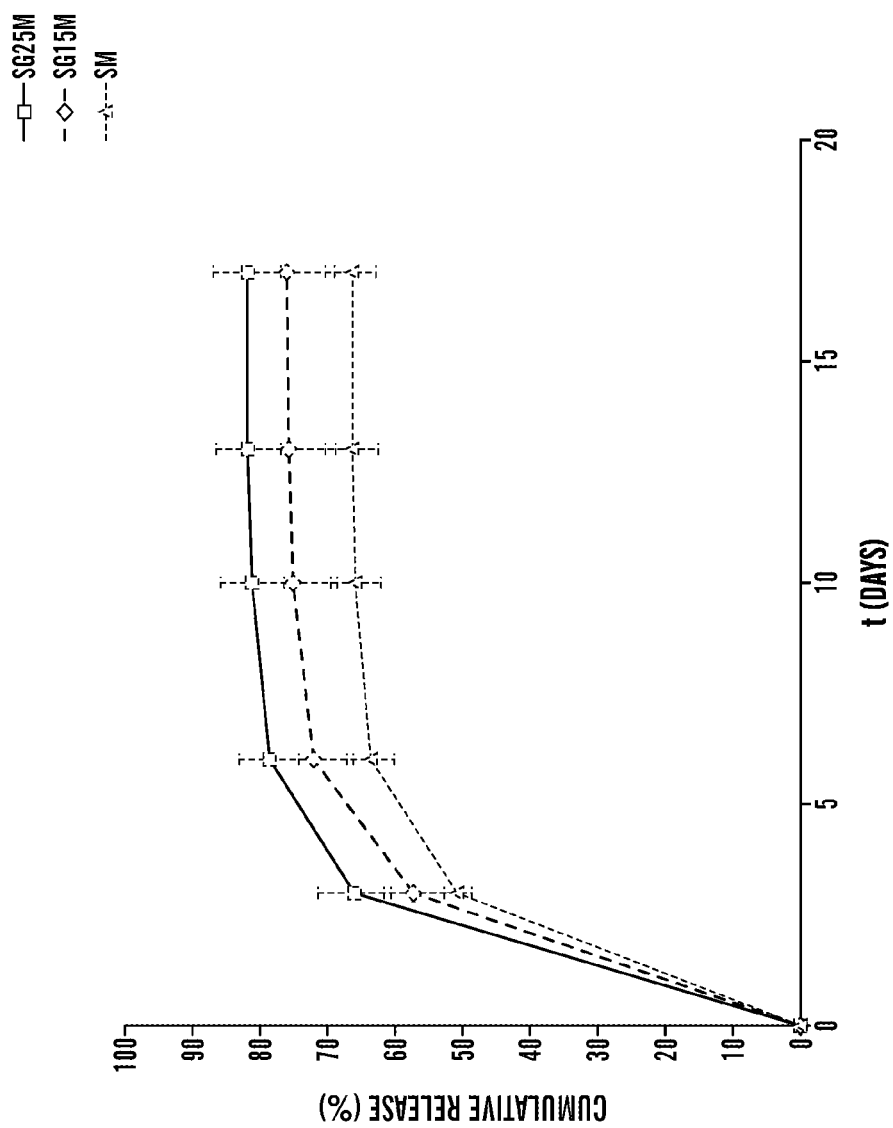
FIG. 5 is a line graph showing memantine release from silk SCFD microspheres having different silk/glycerol ratios. The SG25M samples contained 25% (w/w) glycerol (silk/glycerol=~3/1); the SG15M samples contained 15% (w/w) glycerol; and the SM samples contained no glycerol.

FIG. 5 shows the release kinetics of an FDA approved drug for treatment of Alzheimer's disease (Memantine, e.g., NAMENDA®; MW (Memantine hydrochloride)=215.76 g/mole, water solubility 50 mg/mL) from SCFD microspheres prepared from ~5% silk solutions having different glycerol contents (0%, ~15% and ~25% glycerol) at ~25% sonication amplitude and ~0.17 mL/min flow rate (Table 2). For the assessed formulations, as indicated in FIG. 5, the release of memantine was sustained for at least over 17 days. The initial burst, e.g., the percentage of the encapsulated drug initially released from the SCFD microsphere (e.g., measured at the first time point (3 days) as shown in FIG. 5), and the cumulative percentage of drug released after 17 days were the lowest in the case of silk-alone SCFD spheres (e.g., silk SCFD spheres without glycerol), while both the initial burst (~50.8%, ~57.4% and ~67.3% for 0%, ~15% and ~25% glycerol, respectively) and the cumulative release after 17 days (~66.4%, ~76% and ~81.9%, for 0%, ~15% and ~25% glycerol, respectively) increased with increasing glycerol content. Unexpectedly, silk/memantine SCFD microspheres were less soluble, e.g., in the release medium, than silk SCFD microspheres prepared without memantine. This indicates that memantine encapsulated in the silk SCFD microspheres can increase the overall beta-sheet crystalline content and/or decrease the water solubility of the microspheres. Furthermore, the data shown in FIG. 5 indicates that the release kinetics of a drug, e.g., an FDA approved small drug, can be controlled effectively, at least partly, via the glycerol content in the formulation. Other factors that can affect small drug release kinetics include, but are not limited to, drug loading, silk concentration, or a combination thereof.

Avastin-Silk SCFD Microspheres.

Figure 6:
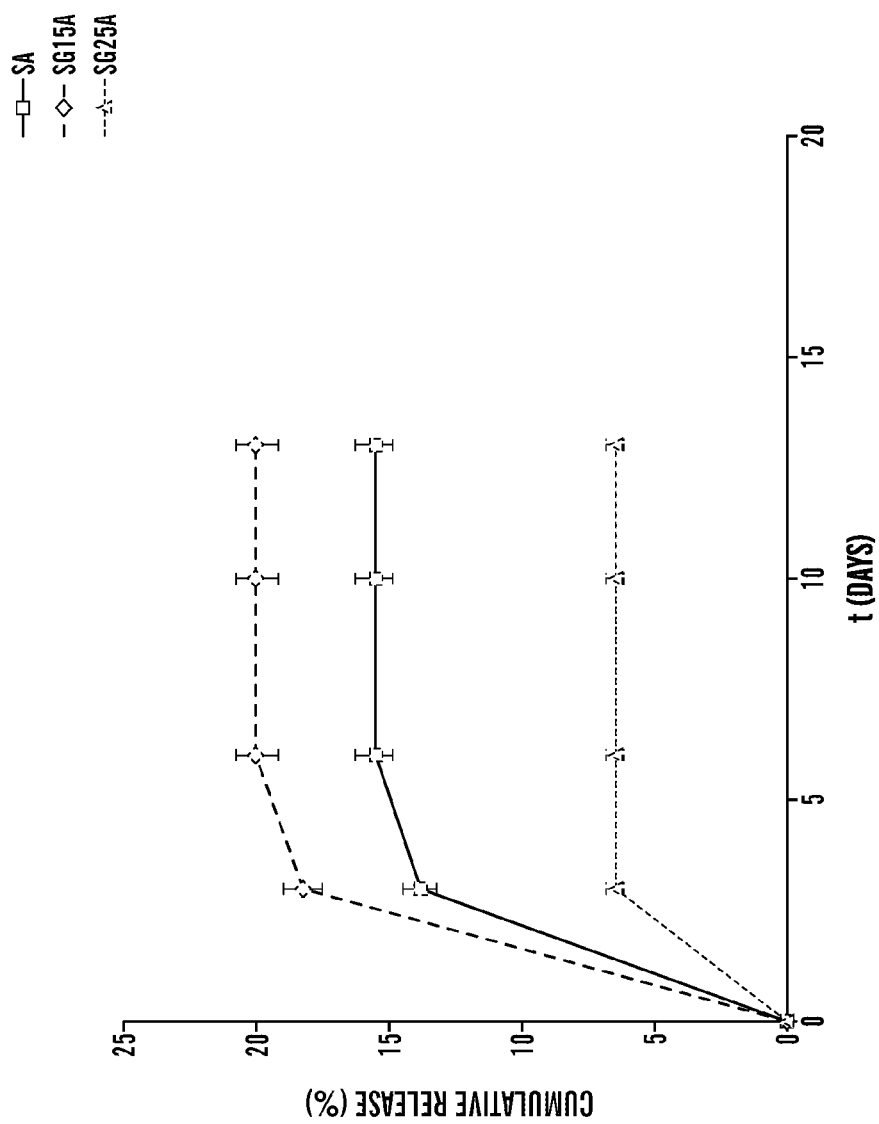
FIG. 6 is a line graph showing bevacizumab release from silk SCFD microspheres having different silk/glycerol ratios. The SG25A samples contained 25% (w/w) glycerol (silk/glycerol=3/1); the SG15A samples contained 15% (w/w) glycerol; and the SA samples contained no glycerol.

FIG. 6 shows the release kinetics of an FDA approved drug for treatment of age-related (wet) macular degeneration (Bevacizumab, e.g., AVASTIN®; MW=149 KDa, ~25 mg/ml stock solution) from SCFD microspheres prepared from ~5% silk solutions having different glycerol contents (0%, ~15% and ~25% glycerol) at ~25% sonication amplitude and ~0.17 mL/min flow rate (Table 2). Compared to preparation of memantine-encapsulated SCFD silk microspheres, the silk/bevacizumab solution was more prone to gelation or aggregation during sonication when making bevacizumab-encapsulated SCFD silk microspheres, indicating a stronger intermolecular interaction between the silk and bevacizumab molecules. Furthermore, both the initial burst (13.8%, 18.3% and 6.5% for 0%, ~15% and ~25% glycerol, respectively) and the cumulative release from bevacizumab-silk microspheres after 13 days (15.6%, 20% and 6.5%, for 0%, ~15% and ~25% glycerol, respectively) were significantly lower than those from memantine-silk microspheres (FIG. 6). In addition, increasing the glycerol content in bevacizumab-silk microspheres to about 25% did not show a trend of increasing the drug release rate, as compared to the release from memantine-silk microspheres. The bevacizumab-silk microspheres with the highest glycerol content (~25%) showed the lowest level of initial burst and the lowest sustained release after 13 days, as compared to the bevacizumab-silk microspheres with 0% or about 15% glycerol content (FIG. 6). Without wishing to be bound by theory, it is likely that a high concentration of glycerol (rich hydroxyl groups) could reinforce the interaction between bevacizumab and silk through hydrogen bonding. The strong binding of protein molecules to silk materials has been previously reported but the underlying mechanism is not yet clear (Wang X. et al. "Silk microspheres for encapsulation and controlled release." J Control Release (2007) 117:360-70 Wang X et al. "Silk nanospheres and microspheres from silk/PVA blend films for drug delivery." Biomaterials (2010) 31:1025-1035; Lu Q. et al. "Stabilization and release of enzymes from silk films." Macromol Biosci (2010) 10:359-368). Due to the overall hydrophobic nature of silk materials, hydrophobic interactions were contemplated to be the predominant force for the binding, even though electrostatic interactions (the pi value of silk fibroin is about 3) and hydrogen bonding can also play important roles (Lu Q. et al., Id). In some embodiments, adjusting other factors that can influence intermolecular interaction between silk and protein drugs (e.g., bevacizumab), including, but not limited to, silk concentration and/or the presence of affinity-interfering additives, can control release of protein drugs from silk material carriers.

Example 5. Syringe Injectability of Silk SCFD Microspheres

Lyophilized silk microspheres, or silk-drug microspheres (e.g., silk-memantine and silk-bevacizumab microspheres) were able to be suspended in about 1% to about 3% sodium carboxymethylcellulose solutions (CMC, viscosity=50-200 cP for 4% solution in water, 25° C.), forming homogeneous suspensions. The CMC suspension of the silk microspheres, including silk-drug microspheres, can be injected through a needle depending on size of the silk microspheres, e.g., a 21 gauge needle, indicating the feasibility of applying silk SCFD microsphere formulation through non-invasive administration routes, e.g., subcutaneous, intramuscular injections, for clinical applications.

Silk microspheres prepared through a novel spray-crystallize-freeze-drying method described herein can preserve their size (~50-~100 μm) and microspherical morphology upon hydration. In some embodiments, a beta-sheet structure-inducing additive, e.g. glycerol, can be blended with silk prior to preparation of silk microspheres, further preserving their size and morphology upon hydration. The methods of producing silk microspheres described herein are time, energy and cost efficient, thus suitable for large-scale production of silk microspheres. In some embodiments, the methods described herein can all-aqueous processes. In some embodiments, high temperature and/or organic solvents are not needed during the methods described herein (e.g., all-aqueous processes), thus allowing encapsulation of sensitive or labile drugs (e.g., heat-labile drugs) at a high yield (e.g., up to 100%). The porous nature of the microspheres described herein can increase the surface area available for drug release. The SCFD microsphere preparation methods can be modified readily, within one of skill in the art, to optimize the drug loading and release profile of a specific therapeutic drug.

REFERENCES

[1] Chiellini F, Piras A M, Errico C, Chiellini E. Micro/nanostructured polymeric systems for biomedical and pharmaceutical applications. Nanomed 2008; 3:367-93.
[2] Ranade V V, Hollinger M A. Drug delivery systems. 2nd ed. Boca Raton: CRC Press, 2004.
[3] Ye M, Kim S, Park K. Issues in long-term protein delivery using biodegradable microparticles. J Control Release 2010; 146:241-260.
[4] Omenetto F G, Kaplan D L. New opportunities for an ancient material. Science 2010; 329:528-531.
[5] Leal-Egaña A, Scheibel T. Silk-based materials for biomedical applications. Biotechnol Appl Biochem 2010; 55:155-167.
[6] Rajkhowa R, Wang L, Wang X. Ultra-fine silk powder preparation through rotary and ball milling. Powder Technol 2008; 185:87-95.
[7] Rajkhowa R, Gil E S, Kluge J, Numata K., Wang L, Wang X, Kaplan D L. Reinforcing silk scaffolds with silk particles. Macromol Biosci 2010; 10:599-611.
[8] Rockwood D N, Gil E S, Park S H, Kluge J A, Grayson W, Bhumiratana S, Rajkhowa R, Wang X, Kim S J, Vunjak-Novakovic G, Kaplan D L. Ingrowth of human mesenchymal stem cells into porous silk particle reinforced silk composite scaffolds: An in vitro study. Acta Biomater 2011; 7:144-151.
[9] Hino T, Shimabayashi S, Nakai A. Silk microspheres prepared by spray-drying of an aqueous system. Pharm Pharmacol Commun 2000; 6:335-339.
[10] Yeo J H, Lee K G, Lee Y W, Kim S Y. Simple preparation and characteristics of silk fibroin microsphere. Eur Polym J 2003; 39:1195-1199.
[11] Wenk E, Wandrey A J, Merkle H P, Meinel L. Silk fibroin spheres as a platform for controlled drug delivery. J Control Release 2008; 132:26-34.
[12] Wang X, Wenk E, Matsumoto A, Meinel L, Li C, Kaplan D L. Silk microspheres for encapsulation and controlled release. J Control Release 2007; 117:360-70.
[13] Wang X, Wenk E, Zhang X, Meinel L, Vunjak-Novakovic G, Kaplan D L. Growth factor gradients via microsphere delivery in biopolymer scaffolds for osteochondral tissue engineering. J Control Release 2009; 134:81-90.

[14] Wang X, Yucel T, Lu Q, Hu X, Kaplan D L. Silk nanospheres and microspheres from silk/pva blend films for drug delivery. Biomaterials 2010; 31:1025-1035.

[15] Suckow R F, Zhang M F, Collins E D, Fischman M W, Cooper T B. Sensitive and selective liquid chromatographic assay of memantine in plasma with fluorescence detection after pre-column derivatization. J Chromatogr B Biomed Sci Appl 1999; 729:217-224.

[16] Wang X, Kluge J A, Leisk G G, Kaplan D L. Sonication-induced gelation of silk fibroin for cell encapsulation. Biomaterials 2008; 29:1054-64.

[17] Lu S, Wang X, Lu Q, Zhang X, Kluge J A, Uppal N, Omenetto F, Kaplan D L. Insoluble and flexible silk films containing glycerol. Biomacromolecules 2010; 11:143-150.

[18] Lu Q, Wang X, Hu X, Cebe P, Omenetto F, Kaplan D L. Stabilization and release of enzymes from silk films. Macromol Biosci 2010; 10:359-368.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of preparing a silk microsphere, the method comprising:
    atomizing a silk solution into individual droplets to form silk microspheres with a diameter of at least 50 µm;
    freezing the silk microspheres, and
    lyophilizing the silk microspheres to form porous silk microspheres, wherein the porous silk microspheres have a porosity of at least 30%.

2. The method of claim 1, wherein atomizing comprises spraying, exposure to coaxial air flow, exposure to mechanical disturbance, and/or exposure to electrostatic force.

3. The method of claim 1, wherein freezing is selected from the group consisting of exposure to sub-zero temperatures and contacting with a cooling agent.

4. The method of claim 1, wherein the silk microsphere is exposed to the sub-zero temperature by collecting the silk microsphere in a container cooled by a cooling agent.

5. The method of claim 1, wherein the silk microsphere is not subject to any post treatment step.

6. The method of claim 5, wherein the silk microsphere has a water solubility of less than 30%.

7. The method of claim 6, wherein the silk microsphere is substantially insoluble.

8. The method of claim 1, wherein the silk microsphere has a beta sheet crystalline content of at least 20%.

9. The method of claim 1, wherein the silk microsphere is not exposed to any non-aqueous solutions.

10. The method of claim 1, further comprising subjecting the porous silk microspheres to a post-treatment.

11. The method of claim 10, wherein the post-treatment is selected from the group consisting of water annealing, water vapor annealing, solvent immersion, heat annealing, and any combination thereof.

12. The method of claim 1, wherein the porous silk microspheres have a porosity of at least 50%.

13. The method of claim 1, wherein the porous silk microspheres have a porosity of at least 80%.

14. A method of preparing a silk microsphere, the method comprising the following steps:
    a) inducing formation of beta-sheet structures in a silk solution;
    b) subsequent to step a), atomizing the silk solution into individual droplets to form silk microspheres with a diameter of at least 50 µm;
    c) freezing the silk microspheres, and
    d) lyophilizing the silk microspheres to form porous silk microspheres, wherein the porous silk microspheres have a porosity of at least 30%.

* * * * *